US012036346B2

(12) United States Patent
Lindo et al.

(10) Patent No.: US 12,036,346 B2
(45) Date of Patent: Jul. 16, 2024

(54) AUTOMATED PERITONEAL DIALYSIS DEVICE

(71) Applicant: Simergent LLC, Chicago, IL (US)

(72) Inventors: Steve J. Lindo, Chicago, IL (US); Cameron Eckert, Markle, IN (US); Emily Byrne, Minneapolis, MN (US); Erika Mallery, Oklahoma City, OK (US); Richard Pendergraft, Norman, OK (US); Jacob Henderson, Oklahoma City, OK (US)

(73) Assignee: Simergent LLC, Chicago, IL (US)

( * ) Notice: Subject to any disclaimer, the term of this patent is extended or adjusted under 35 U.S.C. 154(b) by 440 days.

(21) Appl. No.: 17/222,208

(22) Filed: Apr. 5, 2021

(65) Prior Publication Data

US 2022/0313882 A1    Oct. 6, 2022

(51) Int. Cl.
*A61M 1/28* (2006.01)
*A61M 1/00* (2006.01)
*G01G 23/00* (2006.01)

(52) U.S. Cl.
CPC .............. *A61M 1/28* (2013.01); *A61M 1/282* (2014.02); *A61M 1/69* (2021.05); *G01G 23/005* (2013.01); *A61M 2205/36* (2013.01)

(58) Field of Classification Search
CPC ....... G01G 23/005; A61M 1/28; A61M 1/282; A61M 1/69; A61M 2205/36
USPC .......................................................... 177/187
See application file for complete search history.

(56) References Cited

U.S. PATENT DOCUMENTS

| 4,726,435 | A | * | 2/1988 | Kitagawa | G01G 23/06 177/229 |
| 4,899,840 | A | * | 2/1990 | Boubille | G01G 19/083 177/139 |
| 5,096,007 | A | * | 3/1992 | Burkhard | G01G 23/005 177/187 |
| 5,600,104 | A | * | 2/1997 | McCauley | G01G 19/12 177/136 |
| 5,721,398 | A | * | 2/1998 | Balsen | G01G 23/005 177/186 |
| 6,340,799 | B1 | * | 1/2002 | Hama | G01G 21/23 177/184 |
| 6,573,462 | B1 | * | 6/2003 | Shymko | G01G 23/002 177/DIG. 9 |
| 7,836,997 | B2 | * | 11/2010 | Takayasu | B60N 2/90 177/144 |
| 11,013,666 | B2 | * | 5/2021 | Biehl | G01G 17/04 |

(Continued)

OTHER PUBLICATIONS

Overload Protection—Good protection for Load Cells: https://www.hbm.com/en/3541/overload-protection-good-protection-for-load-cells/.

*Primary Examiner* — Randy W Gibson
(74) *Attorney, Agent, or Firm* — Stephen T. Scherrer; Monique A. Morneault; Scherrer Patent & Trademark Law, P.C.

(57) ABSTRACT

The present disclosure relates to an automated peritoneal dialysis (APD) system using gravity to deliver fluid from one or more source dialysate bags to the patient as the destination. The present disclosure further relates to a load cell protection assembly that prevents the load cells associated with the delivery of fluid in the system from experiencing an overload condition in either the down direction or the up direction, while maximizing safety and efficiency of the system while minimizing excess cost and complexity.

8 Claims, 20 Drawing Sheets

(56) References Cited

U.S. PATENT DOCUMENTS

| | | | |
|---|---|---|---|
| 2005/0103535 A1* | 5/2005 | Honda | G01G 21/23 177/202 |
| 2007/0135779 A1 | 6/2007 | Lalomia et al. | |
| 2012/0283629 A1 | 11/2012 | Childers et al. | |
| 2014/0088493 A1 | 3/2014 | Pan | |
| 2014/0316332 A1 | 10/2014 | Lo et al. | |
| 2020/0261638 A1 | 8/2020 | Lindo et al. | |

* cited by examiner

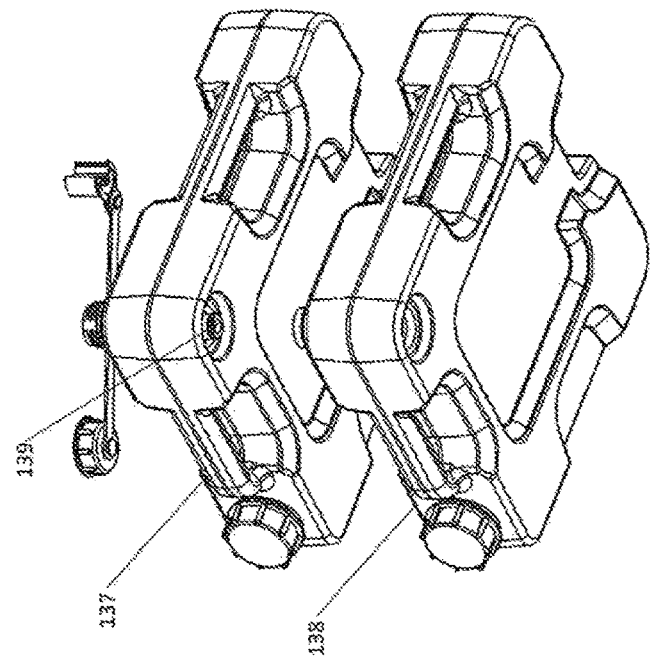
FIG. 24b
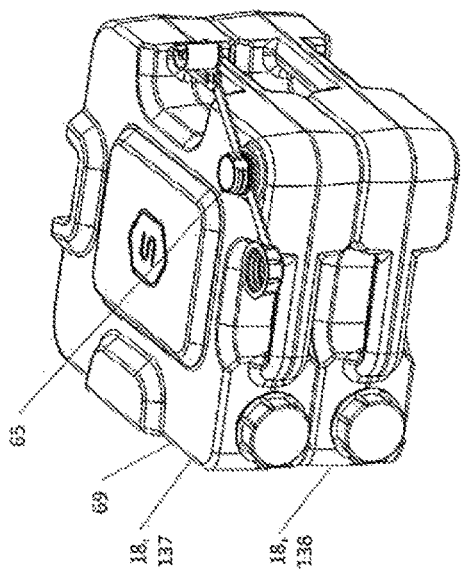
FIG. 24
FIG. 24a

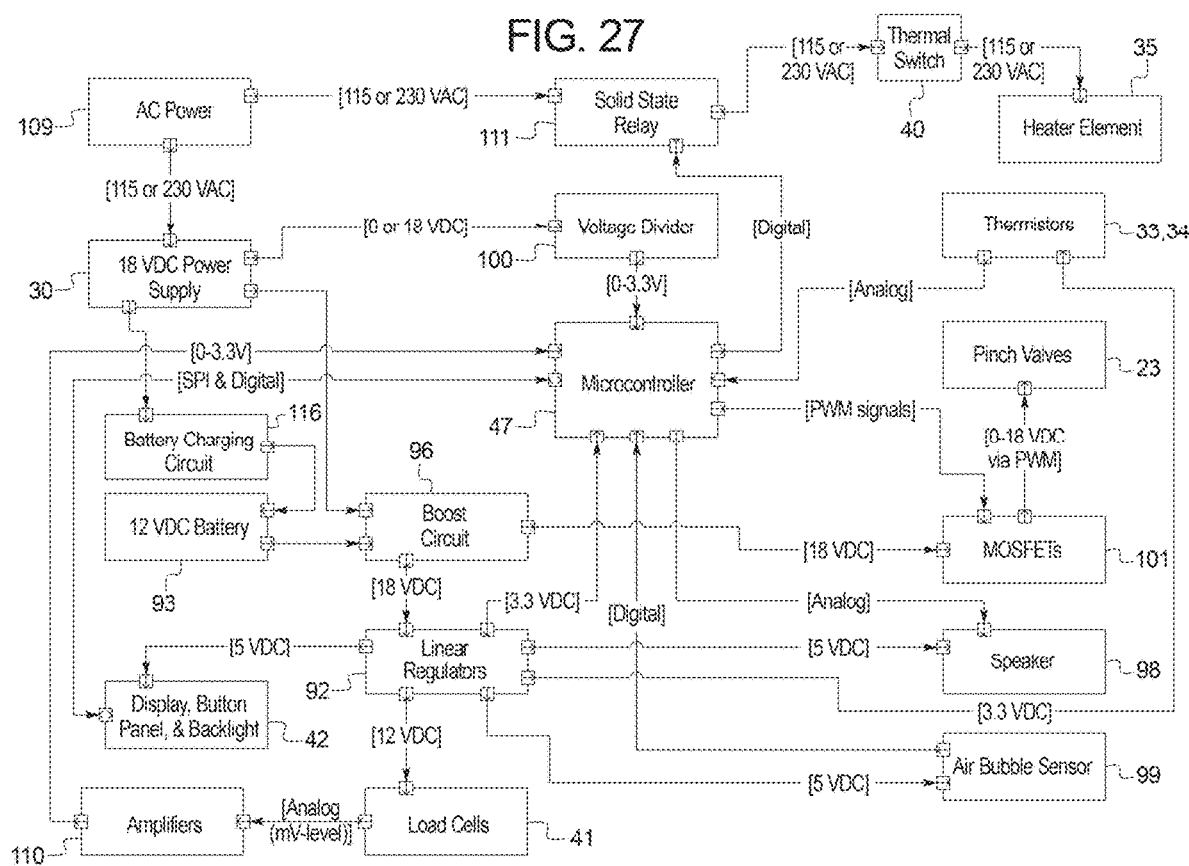

AUTOMATED PERITONEAL DIALYSIS DEVICE

TECHNICAL FIELD

The present subject matter relates generally to automated peritoneal dialysis (APD) devices, and potentially may be applied to other medical device applications as well, including hemodialysis applications.

BACKGROUND

Peritoneal dialysis (PD) consists of a series of cycles of filling, dwelling, and draining dialysate solution into and out of a patient's peritoneal cavity in their lower abdomen for patients with End Stage Renal Disease (ESRD). The solution is exchanged by connecting one or more dialysate solution bag(s) and associated disposable tubing to a transfer set with a shutoff pinch valve, which in turn connects to a PD catheter surgically implanted in the patient's abdomen. PD dialysate solution contains dextrose, icodextrin (i.e., starch-derived glucose polymer), or other molecules to create an osmotic gradient which allows toxins and excess fluids in the bloodstream to transport through the peritoneal membrane's capillary walls and into the dialysate solution. PD dialysate solution also contains electrolytes to maintain patients' normal blood composition. PD dialysate solution is currently commercially available in three different dextrose concentrations and a single icodextrin concentration.

PD therapy is performed either via gravity with dialysate bag(s) hung on a pole or elevated shelf, or with a device (cycler) to provide the motive fluid pressure/suction, also known as Automated Peritoneal Dialysis (APD). APD therapy is typically performed for 8-10 hours each night while the patient sleeps. Dialysate bags are typically hung or placed at the beginning of therapy and are typically removed after therapy completion. The patient and/or a family member or caregiver typically sets up the APD device, its associated disposable tubing set, and PD dialysate bags each night before commencing therapy.

Today, active pumping APD devices are expensive, with significant costs associated with the pump, valves, pressure sensors, and/or pneumatic manifolds, along with significant costs associated with the disposable tubing sets with cassettes to interface with said APD devices. Additionally, excessive delivery and/or suction pressures causes inflow or outflow pain during filling or draining phases for many patients. For both of those reasons, gravity-based APD devices offer benefits over current active pumping APD devices.

Today, active pumping APD devices' disposable tubing sets with cassettes are expensive. Some cassettes may require expensive ultrasonic welding or other technology to bond a rigid plastic cassette with a flexible thin plastic sheeting membrane, with costly high scrap rates associated with failed sheeting bonds. An APD device's disposable tubing set without a cassette offers cost benefits over traditional cassette-based tubing sets.

Conventionally, active pumping APD device systems, when combined with the requisite dialysate bags, are oriented in a horizontal fashion when set up in the patient's home. The APD device is typically placed on a stationary nightstand or large cart, with one or more PD dialysate bags placed next to the APD device to achieve the typical 10,000 mL-15,000 mL delivery volumes via multiple bags, each typically ranging in volume from 2,000 mL to 6,000 mL. A typical configuration might be one 5,000 mL bag placed on the APD device as a heater bag, one additional 5,000 mL bag (supply bag) placed next to the APD device, and another 2,000 mL bag (last fill bag) also placed next to the APD device. An APD device with integrated wheels and vertically-oriented dialysate bag mounting structure provides mobility benefits over current active pumping APD devices because the entire system takes up a smaller footprint on the floor and is thus more easily transported throughout the patient's home than active pumping devices mounted on a nightstand or large cart.

Patients and health care providers may desire for APD devices to be portable, both within the home and outside the home. For gravity-based devices, portability poses a problem since the machines tend to be rather tall in their therapy operational position.

Free flow of fluid from an APD device resulting in unintended Increased Intraperitoneal Volume (IIPV) can be fatal to patients. As such, there is a need for mechanisms to prevent free flow during certain single-fault conditions, such as loss of power to one or more valves which control fluid flow to or from the patient.

Conventionally dialysate bags are often difficult to lift up to place them in the proper position required for therapy. Dialysate bag volumes may reach or exceed 6000 ml, with corresponding weights of approximately 61 Newtons (13.7 lb). These bags typically must be lifted from their original shipping container(s) (e.g. cardboard box) from approximately ground level to either approximately waist height for active pumping APD devices, or from ground level to 1.2-1.9 meters above ground level for gravity-based APD devices, in order to achieve the necessary head height required for appropriate therapeutic flow rates. In addition, the peritoneal dialysis patient population tends to skew older and more frail than the general population, thus exacerbating these potential lifting difficulties. Lifting heavy dialysate bags may cause shoulder or back problems, may lead to the user losing balance and/or falling over. These same difficulties may be experienced by caregivers who may perform setup rather than the patients themselves. Additionally, patients and caregivers in certain regions in the globe and/or female patients may have smaller statures and may not have as much strength as others. Additionally, many PD patients also suffer from other comorbidities or illnesses such as diabetes mellitus, which may further reduce the patient's ability to lift heavy objects.

Some manufacturers may instruct patients to use several smaller dialysate bags (e.g. 2000-2500 ml each) rather than fewer larger bags (5000-6000 ml each) for ease of lifting. However, several smaller bags are more expensive to manufacture than fewer larger bags. Additionally, several smaller bags may take up more room on the surface on which the bags are placed (e.g. table, cart, nightstand, etc).

Some manufacturers have attempted to mitigate the height required to lift the bags for gravity-based APD therapy by placing the bag hooks/shelves at a lower height than they would otherwise want to place them to achieve good flow rates. These approaches may be used for either active pumping or gravity-based APD devices.

If a gravity-based APD device provides a lower-than-optimal placement height for the dialysate bags, the flow rates for delivering fresh dialysate solution to the patient may be reduced. This will either result in a longer therapy duration or less effective therapeutic outcomes.

A PD therapy consists of several cycles of fill, dwell, and drain. The exchange of toxins and excess fluid from the patient's bloodstream occurs primarily during the dwell periods. If it takes longer to fill due to suboptimal dialysate bag head height, then there may be less time available for dwelling. Diffusion and osmosis occurs between the patient's peritoneal membrane and the solution dwelling in contact with that membrane, after having been filled from the APD device. Therefore, therapy is less effective if low flow rates result in less dwell time, for a given (e.g. 8 hour) total therapy time. Alternatively, low flow rates could lead to longer total therapy duration, which is not desirable since patients' lives are disrupted with therapy durations that exceed the patient's normal nocturnal sleep duration.

Current APD devices offer an option to drain the spent effluent into a disposable drain container, typically constructed of flexible plastic film with inlet and/or outlet ports bonded into the bag. There is a need for a reusable drain container which is not frequently discarded to reduce cost and improve the environmental impact of the extra plastic drain container typically discarded each day.

Additionally, APD users may have difficulty draining the relatively large fluid volumes that may be stored in one or more reusable or disposable drain containers if the drain containers do not contain features to facilitate easy drainage.

Additionally, APD users may have difficulty lifting a single drain container whose capacity can reach 15-20 L or greater, with a corresponding mass of 15-20 kg or greater. There is a need for a reusable drain container(s) which weighs significantly less than 15-20+ kg.

Some APD users may have difficulty attaching one or more control or measurement modules to a vertical pole structure for gravity-based APD devices. Difficulties may lie in attempting to hold a module in one hand while using a tool in the other hand to attach the module to the pole structure, such as a screwdriver, Allen wrench, or pole clamp knob. Additionally, some users may not be familiar with certain tools. Others may not have the hand strength or dexterity to use said tools due to the patients' advanced age and/or frailty due to complications associated with the patients' kidney disease or other comorbidities. Those users who are themselves patients frequently suffer from diabetic neuropathy, which can affect the dexterity in their fingertips, thus making it more difficult to use hand tools. There is a need for a vertical pole structure and associated modules which do not require any tools to assemble the modules to the pole nor to disassemble the modules for travel or for transporting the APD cycler to and from the manufacturer or servicing center.

Some APD users may have difficulty reaching the hooks of an IV pole to mount a large (5 L or 6 L) bag for gravity APD usage, when those hooks are mounted to the height required to achieve good flow rates even when the bag is almost empty, which is a function of the height from the patient's abdomen (bed height) to the bottom of the bag intended for delivery (heater bag). Further, if gravity is to be used to replenish the heater bag from one or more supply bags and/or a last fill bag, if the bags are mounted in a vertical orientation, this requires the bottom of the supply bag and last fill bag to be mounted above the top of the heater bag, thus further increasing the height required for the user to lift the supply bag and last fill bag. For users shorter in stature, this problem of placement of bags at high heights is further exacerbated. As such, there is a need for a pole/cart which minimizes the height required for placing the heater bag, supply bag, and last fill bags, while maintaining the height of the bottom of the supply and last fill bags above the top of the heater bag.

If the supply bag and last fill bag are placed on a shelf directly above the heater bag, it may be difficult to access the heater bag to place it on the heater surface prior to therapy or to remove it after therapy. There is a need for a pole/cart that minimizes the height of the supply bag and last fill bag shelf, while allowing the user to easily access the heater bag, without interference from the supply and last fill bag shelf.

Some gravity-based APD devices integrate the user interface with the heater unit. Because the heater bag placed on the heater unit must be mounted at a height substantially above the bed, the user interface may not be easily readable from the patient's bed while lying down. There is a need for a user interface that can be adjusted to be mounted close to the same height as the bed, or just above the bed height, separate from the heater unit.

Some APD devices use load cells to weigh the fluid prior to delivery to the patient and/or the fluid drained from the patient to a drain receptacle. Historically, APD devices using load cells have experienced poor reliability due to frequent load cell overload failures. Load cells contain sensitive components, which can include strain gages, and are sensitive to failure or permanently reduced accuracy as a result of overload conditions. Some load cells experience permanent damage when subjected to as little as 20% beyond their full-scale load rating. This overtravel limit can be exceeded by pressing in the normal (down) direction of a load cell, or in the up direction if the weighing platform or its associated structure above the load cell is affixed to the top surface of the load cell, for instance, if the user accidentally lifts up on the platform, bumps the platform upward, or if the platform experiences excessive vibrations during shipping and transport or as a result of dropping the dialysate bag or drain container onto the load cell, which can result in both up and down vibrations. Load cells are inexpensive and normally very accurate when not overloaded, however, and thus are desirable components to use for weighing dialysate fluid in APD devices. As such, there is a need for a load cell implementation that prevents the load cell from experiencing an overload condition in either the down direction or the up direction, while minimizing excess cost and complexity.

Patients and health care providers desire for APD devices to be portable, affordable, easy to clean, and aesthetically pleasing. Accordingly, there is a need for a system that addresses problems associated with active pumping devices, device/pole/cart assembly/adjustability/disassembly, APD cassettes, peritonitis, loading dialysate bags, horizontal device footprint, user interface readability, portability, free flow/IIPV, dialysate bag lifting problems, low literacy users, low flow rates, therapy efficacy, lifting and draining spent effluent, and load cell reliability, while providing a cost effective means to deliver good dialysate flow rates with accurate volumetric measurement to encourage fast fill cycles, resulting in a safe, efficient and effective therapy.

SUMMARY

To meet the needs described above and others, the present disclosure provides multiple solutions to the problems of peritonitis, active pumping devices, APD cassettes, loading dialysate bags, horizontal device footprint, free flow/IIPV, dialysate bag lifting problems, low flow rates, therapy efficacy, portability, drain containers, and load cell damage to encourage easy device and disposables setup and teardown, increased device reliability, and prevent unnecessary injuries.

In satisfaction of this and related objects, the present system provides an improved automated peritoneal dialysis device which is unique in its design, manufacturability, and its capacity to serve as an automated peritoneal dialysis device in a cost-effective manner.

An automated peritoneal dialysis (APD) system using gravity to deliver fluid from one or more source dialysate bags to the patient as the destination, and using gravity to deliver fluid from the source patient to the destination drain container or drain receptacle, and heats at least one dialysate bag placed onto a heated plate, and using a disposable tubing set for dialysate delivery to and from the patient, and using one or more solenoid-operated, normally closed, electronically-controlled pinch valves which pinch or release the disposable tubing set's tubing to stop or start fluid flow, respectively.

The system can include a heater bag that can be heated via a heater element separated from a metal heater plate by a layer of flexible rubber and one or more layers of electrically insulated polyamide film.

The source dialysate bags may include a heated bag and a non-heated supply bag which may be replenished into the heated bag such that replenishment fluid flow is controlled via a dedicated Supply replenish pinch valve which is in turn controlled via a microcontroller. The supply bag may contain dextrose (or any suitable solution), commonly used for APD therapy.

An additional source dialysate bag may include a unique last fill bag which is replenished into the heater bag prior to delivery of the last fill before the patient is to disconnect from the system for the long daytime dwell period such that replenishment fluid flow is controlled via a dedicated Last Fill replenish pinch valve which is in turn controlled via a microcontroller. The additional last fill source dialysate bag may contain icodextrin (or any suitable solution), commonly used as the last fill solution in APD therapy. Alternatively, the additional source dialysate bag may contain dextrose similar to that of the supply bag, in which case this additional source dialysate bag can be used as a second supply bag to replenish into the heater bag not only for the optional last fill phase, but also for other therapy fill phases prior to the optional last fill.

The fluid flow from the heated bag to the patient is controlled via a dedicated Patient Fill pinch valve which is in turn controlled via a microcontroller. The fluid flow from the patient to the drain container or drain receptacle is controlled via a dedicated Patient Drain pinch valve which is in turn controlled via a microcontroller.

The fluid volume delivered from the heater bag to the patient can be calculated via weight using one or more load cells, and the fluid volume drained from the patient to the drain destination or drain container is calculated via weight using one or more load cells, wherein the output from all load cells are measured and stored by a microcontroller and its associated memory.

The therapy status information can be displayed via graphical touch screen and therapy programming and user input is entered via graphical touch screen. The therapy setup steps can be displayed using both text and images, conveying loading the heater bag, supply bag, and last fill bag, loading and connecting the disposable tubing set, loading the drain container(s), connecting the drain tube into the drain containers, and connecting the tubing set to the patient's catheter transfer set. These graphical and text instructions on the graphical touch screen can also display teardown steps, conveying closing the patient line and/or transfer set clamps, disconnecting the patient line from the transfer set, emptying the drain container(s), disconnecting the disposable tubing set from the device, and removing the used dialysate bags.

The heater unit and control unit enclosures can be mounted onto, or removable from a cart having at least three wheels and with an integrated, removable vertical pole via toolless quick release mechanisms. The cart contains a weighted base and/or wide enough wheelbase such as such an amount as to mechanically prevent the entire system's center of gravity from exceeding a horizontal distance beyond the center of the furthest wheel when placed at an angle of at least 5' from horizontal, when the maximum number of the maximum volume of permissible dialysate bags are loaded in their highest permissible height configuration for transport and the drain container is empty. The dialysate bag (heater bag) may be placed onto the first enclosure which heats the bag to approximately body temperature as measured by one or more temperature sensors. The first enclosure (heater unit) is mounted above the patient's bed surface, while the second enclosure (control unit) having a touch screen display, is mounted below the first enclosure. One or more reusable drain containers may be placed onto a third enclosure or platform (drain unit), which weighs the drain container via one or more load cells. The third enclosure is mounted below the second enclosure and below the patient's bed surface. The drain unit is integrated into the cart's base and is not removable.

The one or more enclosures can be mounted onto the Cart's pole constructed of one or more segments of square or rectangular tubing. One or more quick release bracket platforms can be mounted onto the pole with a square protrusion extending vertically from each bracket platform. The one or more enclosures contain a similarly shaped square socket and associated spring-loaded quick release lever to disengage a latch mechanism from the bracket platform. The bracket platform for mounting the Heater Unit contains a bent sheet metal semi-circular pocket which interfaces with a horizontal rod integrated into the bottom of the Heater Unit such that the rod fits into the pocket first to stabilize the left side of the Heater Unit, then the right side of the Heater Unit is pressed down to engage the square protrusion in the bracket with a latch inside the square socket in the Heater Unit, similar to how a ski boot's back side interfaces with a pocket in the ski before pressing down the front surface of the boot into the ski's latch mechanism. The bracket platform for mounting the Control Unit contains a similar square protrusion, square socket, and quick release lever and latch as described above, without requiring the bent semi-circular pocket or horizontal rod due to the smaller size of the Control Unit. The pole contains multiple holes along a vertical axis along one or more sides of the tubing, wherein one or more enclosure-holding brackets are each mounted to the pole via one or more spring-loaded pin(s) or latch(es) through the aforementioned holes to allow for adjustable height of the bracket(s). One or more of the enclosures mount to the enclosure bracket(s).

The destination drain container can be configured as two stackable or side-by-side reusable plastic containers. The containers are transparent to allow the user to view the color and status of the spent effluent. The drain container can contain a flat side along the side closest to the drain spout opening such that the drain container may be tipped over approximately 90° such that it is resting on its flat side while the fluid contents are drained into a tub, toilet, sink, floor drain or other drain destination.

The destination drain container can be split into a primary and secondary drain container such that spent effluent flows from the disposable tubing set's drain line into the primary drain container, wherein when the primary drain container is filled to approximately 6 L, it spills spent effluent into a secondary drain container. The configuration of these drain containers could be either stackable or side-by-side.

In the stackable drain container embodiment, consisting of a top (primary) drain container and a bottom (secondary) drain container, after the secondary drain container is full (approximately 10.5 L), the primary drain container finishes filling from approximately 6 L to capacity (10.5 L). The valve insert into the bottom of the primary drain container (e.g. male) is different than the valve insert into the top of the secondary drain container (e.g. female) such that when the primary container is inserted downward into the secondary drain container, the primary container's male valve opens a self-closing, spring-loaded female valve in the secondary drain container, similar to the auto-opening and auto-shutting valve in a coffee maker's water reservoir, except that in this disclosure, not only does the primary container's bottom outlet valve close when disconnected, but also the secondary container's top inlet valve closes when disconnected. This ensures that when the two containers are disconnected, the fluid does not leak out of the bottom of the primary container's outlet valve, nor the top of the secondary container's inlet valve. This self-closing feature is additionally desirable since the stackable drain containers are designed with a carrying handle along the side of the drain container so that it has a slimmer profile when carried from the handle in a vertical configuration, rather than attempting to transport it in a horizontal configuration, which would require two-handed carrying. In the vertical carrying position, even the top valve of the secondary drain container could now be immersed in fluid and thus, requires a self-closing valve. The valves contain vent paths so that as the secondary drain container fills, the air above the fluid level in the secondary container is allowed to escape up the secondary container's inlet valve and through the primary container's exit valve. Without that feature, once the secondary container reaches a certain amount of air pressure that exceeds the head pressure of the fluid above it, all fluid ceases to flow from the primary drain container to the secondary drain container. As a result, the fluid would spill out the top of the primary container prior to the secondary container being completely full of fluid and thus, the total capacity of the drain containers would be reduced to little more than the capacity of the primary container alone.

In the side-by-side drain container embodiment, a connecting tube exits the side wall of each drain container with quick disconnect (QD) self-closing valves within the tube (male end connected to the first drain container's tube, and the female end connected to the second drain container's tube). If the user desires to empty one drain container, the user disconnects the QD and both the male and female ends automatically close off the fluid path to prevent leaks. The disposable tubing set's drain line is inserted into the inlet hole of one of the side-by-side drain containers (primary). In one embodiment, after the primary drain container is filled to approximately 6 L, the fluid level reaches the tube in the sidewall, whereby it begins spilling any additional spent effluent into the secondary drain container until the secondary container reaches approximately 6 L, then both containers fill equally thereafter until approximately 21 L have been filled collectively (10.5 L each). In another embodiment, the connecting tube is inserted into the lower side wall of each drain container such that both drain containers fill equally throughout the therapy as fluid is drained from the patient.

An automated peritoneal dialysis (APD) system which delivers fluid from one or more source dialysate bags to the patient as the destination, wherein a disposable tubing set is used for dialysate delivery to and from the patient, is provided. This APD system delivers spent effluent from the patient to one or more drain container(s), wherein the disposable tubing set is used for effluent delivery from the patient to the drain container(s). The drain container(s) rest on a drain unit containing a load cell which is protected from overload conditions in the up and down directions. The system further includes a source dialysate heater bag that rests on a heater unit platform containing another load cell which is also protected from overload conditions in the up and down directions.

The heater unit connects to the cart by first placing the locator horizontal rod on the underneath side of the heater unit into a corresponding receiver socket of the cart's top bracket (similar to the back end of a typical ski boot), then pressing down on the opposite end of the heater unit such that the protrusion in the cart's top bracket platform inserts into a socket within the heater unit and such that a spring-loaded latch in the heater unit engages with a notch in the side of the protrusion. The heater unit disconnects from the cart by squeezing the quick release latch. Neither connection nor disconnection requires any tools to actuate.

The Control Unit connects to the cart by positioning the Control Unit above the protrusion in the Middle Bracket platform and pressing down on the Control Unit such that the protrusion in the cart's middle bracket platform inserts into a socket within the Control Unit and such that a spring-loaded latch in the Control Unit engages with a notch in the side of the protrusion. The Control Unit disconnects from the Cart by squeezing the quick release latch. Again, neither connection nor disconnection requires any tools to actuate.

The drain unit weighs the contents of the drain container(s) via a load cell rated for a range of 20-50 kg full scale (F.S.) (with maximum safe overload up to 120% of full-scale rating) whose signals are sent to the control unit for processing and controlling fluid flow into or out of the patient by opening and closing pinch valves, which pinch or release the disposable tubing set. This drain unit load cell is mounted atop a bottom steel plate. The underneath surface of the plate contains two vertical down-travel guideposts around each of which a "down-protection" spring is mounted such that the springs sit between the bottom steel plate and a steel base plate. Each of the two vertical guideposts sits within a bushing mounted into the base plate, which is itself mounted on top of the metal cart base frame composed of square steel tubing. This bushing allows the vertical posts to travel up and down freely as the springs are compressed or released.

Two "down stop" cylinders or screws are screwed into the underneath side of a top steel base plate, which sits atop a top mounting plate to which the upper surface of the load cell is attached. The two "down-protection" springs are preloaded to approximately the maximum normal rated operating capacity of the load cell such that the springs do not compress any further during normal down-loading conditions. This preload distance may be calculated using the spring force equation, $F=Kx$, where K is the spring constant and x is the compression distance, and, with a two-spring implementation, for each spring, F=maximum full-scale rated load/2. The spring constant is chosen such that the total deflection from the maximum full-scale rating to the maximum safe overload condition (hard stop) is greater than 1 mm and ideally >3 mm so as to minimize tight adjustment tolerances in the manufacturing assembly process.

When a downward load exceeds approximately 100% of the normal rated operating capacity, but is less than the maximum safe overload condition (e.g. 120% of full-scale rating), the down-protection springs begin compressing beyond their initial pre-loaded condition. At or before the load reaches the maximum safe overload condition (e.g. 120% of full-scale reading), the down stop cylinder contacts the base plate's hard stop.

The down stop cylinder's height above the base plate's hard stop is adjustable up or down by screwing the cylinder clockwise or counterclockwise from the threaded insert in the top steel plate. This gap is adjusted in the factory to ensure it stops at or before reaching the maximum safe overload condition (120% of full-scale rating), while not reaching the hard stop before the desired measurement range which is typically approximately 0 to full scale, or in another embodiment, 0 to slightly less than full scale for load cells which are never intended to reach the full-scale loading during normal loading conditions.

The heater unit of the present system weighs the contents of the heater bag via a load cell rated for a range of 10-30 kg full scale (F.S.) (with maximum safe overload up to 120% of full-scale rating whose signals are sent to the control unit for processing and controlling fluid flow into or out of the heater bag and into the patient by opening and closing pinch valves, which pinch or release the disposable tubing set. The maximum normal use load is 10 kg, when taking into account a maximum 6 kg bag sitting atop other structure with mass <=4 kg.

This heater unit load cell is mounted atop a bottom steel plate. The top surface of the plate contains two vertical down-travel guideposts around each of which a "down-protection" spring is mounted such that the springs sit between the bottom steel plate and a large washer under the bolt head, which may be integrated into the bolt head. Each of the two vertical guideposts sits within a bushing mounted into the base plate, which is itself mounted on top of the heater unit enclosure composed of plastic. This bushing allows the vertical posts to travel up and down freely as the springs are compressed or released. The heater unit enclosure is mounted into the cart via a quick release mechanism.

A steel base plate serves as the "down stop", which comes into contact with the bottom surface of the load cell upon excess loading. The base plate is a bent sheet metal plate in a hat-shape in a preferred embodiment, such that the bottom surface of the hat mounts to the inside bottom surface of the heater unit's plastic enclosure. A top steel base plate sits atop a top mounting plate to which the upper surface of the load cell is attached. The heater bag tray, consisting of an aluminum heater plate and a plastic walls, is mounted atop the top steel plate.

The two "down-protection" springs are preloaded to approximately the maximum expected normal operating load (e.g. >6 kg), which is somewhat less than the maximum normal rated operating capacity of the load cell (e.g. >10 kg) such that the springs do not compress any further during normal down-loading conditions. This preload distance may be calculated using the spring force equation previously described. The spring constant is chosen such that the total deflection from the maximum expected normal operating load to the maximum safe overload condition (hard stop) is greater than 1 mm and ideally >3 mm so as to minimize tight adjustment tolerances in the manufacturing assembly process.

When a downward load exceeds approximately 100% of the normal rated operating capacity, but is less than the maximum safe overload condition (e.g. 120% of full-scale rating), the down-protection springs begin compressing beyond their initial pre-loaded condition. At or before the load reaches the maximum safe overload condition (e.g. 120% of full-scale reading), the down stop cylinder contacts the base plate's hard stop.

The down stop cylinder's height above the base plate's hard stop is adjustable up or down by screwing the cylinder clockwise or counterclockwise from the threaded insert in the top steel plate. This gap is adjusted in the factory to ensure it stops at or before reaching the maximum safe overload condition (120% of full-scale rating), while not reaching the hard stop before the desired measurement range which is typically approximately 0 to full scale, or in another embodiment, 0 to slightly less than full scale for load cells which are never intended to reach the full scale loading during normal loading conditions.

The base plate is used so the entire drain unit may be assembled as a subassembly, making the necessary adjustments to the down stop gap prior to mounting the drain unit to the cart base's lower tubing structure. An alternative embodiment could involve mounting the down springs and associated bushings directly to the cart base lower tubing and omitting the base plate, in which case the cart base lower tubing would serve as the hard stop for the down stop cylinders.

The heater unit enclosure and drain container tray contain walls surrounding the up and down springs and the load cell to protect the springs and load cell from foreign object debris.

In an alternative embodiment, the down stop cylinders could be mounted in different locations and could vary in quantity. Those locations could be on a fixed base plate such that a movable top plate above the load cell comes in contact with the down stop cylinders. They are also not limited to cylindrical shape, but could be any shape which provides a hard surface to prevent further load cell bending upon contact, even if additional load force is applied to the load cell.

In yet another alternative embodiment, the down springs and up springs could be mounted in different locations and could vary in quantity.

In a further alternative embodiment, a single flat spring could be mounted beneath the load cell such that the load cell travels further with an applied load than it would without the flat spring. This flat spring could be mounted such that the load cell extends off the edge of it as if extending off the edge of a diving board, or the spring could be mounted such that the lower mounting point of the flat spring is approximately directly below the upper mounting point of the load cell where it meets the platform being weighed, similar to a Z-shape. In this manner, the total system is more compact and has less total vertical travel at the point of the platform furthest away from the load cell mounting point.

With the flat spring configuration, a down stop may be located directly underneath the load cell. In the unloaded configuration, a gap exists between the load cell and the down stop. At or before reaching the maximum safe overload force, the bottom of the load cell touches the down stop. The down stop need not be located directly under the load cell, nor does the load cell need to serve as the object striking the down stop, but rather, the down stop may be located under any other structure that moves with the load cell, which could include a plate above the load cell.

With the flat spring configuration, an optional up stop may be located above the top steel plate mounted above the load cell. In the unloaded configuration, a gap exists between the bottom surface of the up stop and the top surface of the top steel plate.

Other alternatives include other types of springs not described here which serve the same purpose to increase the distance that the load cell travels during down loading conditions and/or up loading conditions. A further alternative may be no spring at all, with a down stop directly underneath the load cell and/or optional up stop directly above the load cell.

Although binocular beam load cells are shown, other load cell types could be used with a similar implementation, as all load cells involve bending a piece of metal under load, and that bending movement can be stopped in the up or down direction with a set of hard stops, and that bending movement can be increased by using springs to protect in the up or down direction more easily without having to have a hard stop within <1 mm of the unloaded surface of the load cell, weighing platform, or mounting structure.

One alternative may be applying only hard stops and/or springs to protect in the down direction and omitting up springs and up hard stops, as the down direction is most often subject to overloading.

The system can be an automated peritoneal dialysis (APD) system or continuous ambulatory peritoneal dialysis (CAPD) system, hemodialysis system, IV infusion pump, or other medical fluid delivery system with solution weighing system, the system including one or more valves to control fluid delivery routing from solution bag(s) to a patient via disposable set(s) and one or more load cells to measure fluid delivered to and/or from the patient.

The system can alternatively be a pharmacy compounding device or other similar apparatus with solution or pellet drug weighing system, the system including one or more load cells to measure fluid or dry drug solutions to control drug delivery from one or more source containers to one or more destination container(s). The source container(s) may be solution bag(s). The destination container(s) may be solution bag(s), vial(s), syringe(s), or other drug storage container(s).

An object of the system is to provide an improved automated peritoneal dialysis device.

Another object of the system is to provide a gravity-based APD device, which offers cost benefits, less pain during inflow and/or outflow, and which operates at lower absolute value pressures (both inflow and outflow), which has potential to reduce the likelihood of peritoneal membrane damage and associated hernias, pleural effusions, and other peritoneal dialysate fluid leakage outside the peritoneal cavity.

Another object of this system is to provide an APD disposable tubing set without a cassette, which offers cost benefits over traditional cassette-based tubing sets.

Another advantage of this system is to provide an APD device which takes up a small floor footprint within the patient's home.

Another advantage of this system is to provide an APD device which is portable, both within the home and outside the home for travel.

Another advantage of this system is to provide an APD device which minimizes the likelihood of unintended Increased Intraperitoneal Volume (IIPV) and free flow.

Another advantage of the system is it provides better flow rates during filling and draining than other APD devices, which can reduce dwell time and thus total therapy time required to achieve desired efficacy outcomes.

Another advantage of the system is it is easier to drain the contents of the reusable drain container with the use of a valved spigot, vent, and/or handle.

Another advantage of the system is it is easier to mount one drain container onto the other without having to remember to open or close any valves between the drain containers.

Another advantage of the system is the drain container is reusable, thus reducing the cost and environmental impact vs. disposable drain containers.

Another object of the system is to reduce the maximum drain container weight a user is required lift to transport and empty the contents of a reusable drain container.

Another object of the system is to minimize fluid leakage while transporting the drain container(s).

An advantage to the system is it provides an APD device which uses certain off-the shelf components which may include a commercially available load cell to reduce cost.

Another advantage of the system is to increase the reliability of the system, especially as it pertains to load cell failures due to overload conditions in the downward direction.

Another advantage of the system is to increase the reliability of the system, especially as it pertains to load cell failures due to overload conditions in the upward direction, which may be experienced during transport, travel, bouncing/vibrating due to sudden load placement, sudden lifting the load off of the load cell weighing platform, or due to unintended bumping by the user, bystander, or pets.

Another advantage of the system is to protect the springs from foreign object debris.

Another advantage of the system is to minimize weighing platform bounce during transport or due to sudden change in weight, which minimizes erroneous weight measurements, miscalculating fluid filled or drained from the patient, overfilling the patient, and/or associated volume-based alarms.

Another advantage of the system is to allow for easy, toolless assembly and disassembly of the system for initial setup and for transport for travel.

Another advantage of the system is, by incorporating modular Heater Unit and Control Unit enclosures, this minimizes the weight of any single enclosure the user must lift in place during assembly or disassembly.

Another advantage of the system is to minimize interference between the heater bag and in turn, the associated heater unit load cell's weight measurement, with the supply and last fill bag shelf, while minimizing the height required to place those bags.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities, and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIGS. 24 (24a and 24b) illustrates a stackable configuration of reusable drain containers.

FIG. 27 illustrates the electrical power distribution block diagram.

It should be noted that various changes and modifications to the presently preferred embodiments described herein will be apparent to those skilled in the art. Such changes and modifications may be made without departing from the spirit and scope of the present system and without diminishing its attendant advantages.

DETAILED DESCRIPTION

Figure 1:
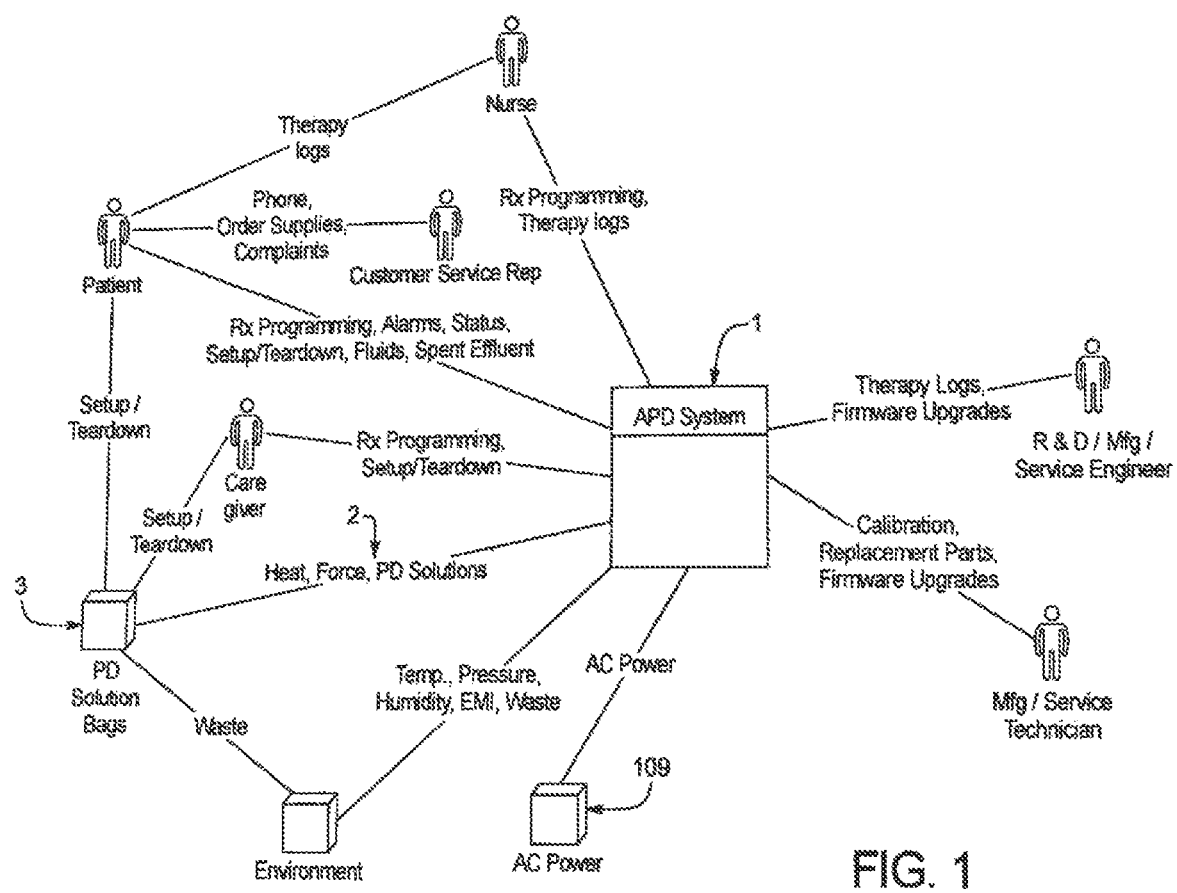
FIG. 1 illustrates a context diagram of an APD system and its external interfaces.
Figure 2:
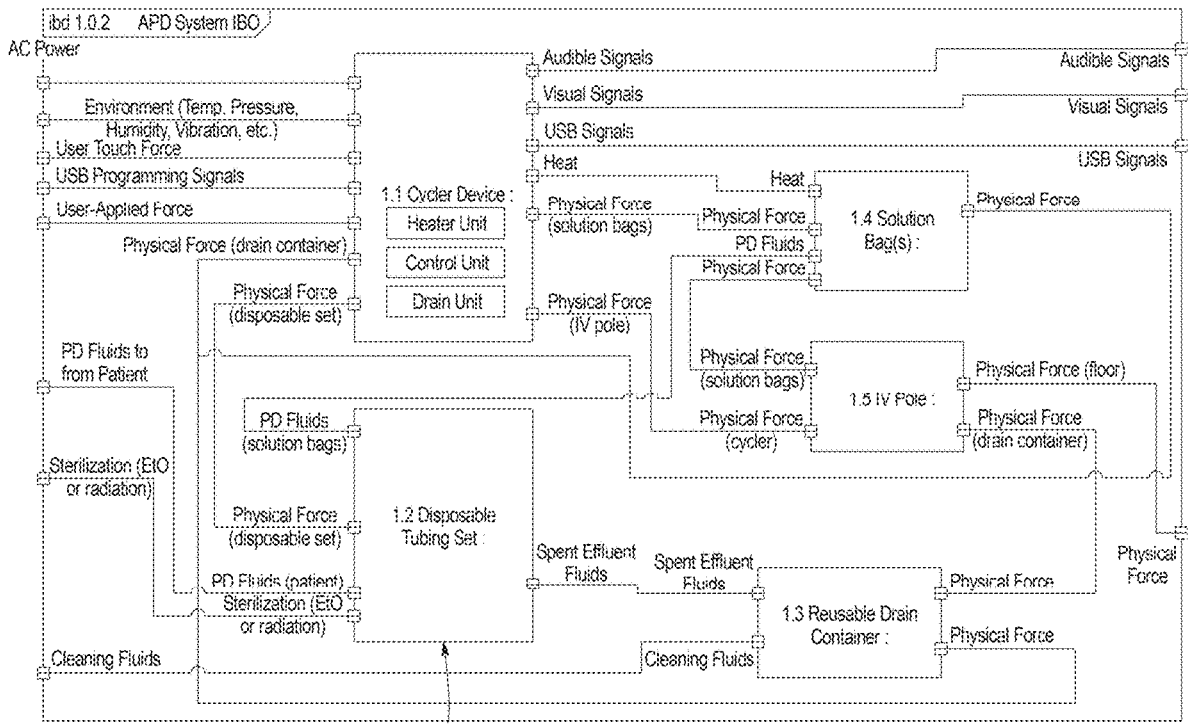
FIG. 2 illustrates an internal block diagram of the major components that make up the APD system.

The present disclosure provides an APD cycler system 1 that delivers APD therapy via gravity dialysate fluid 2 flow through a single use, non-reusable disposable tubing set 7 placed into the cycler's electronically-controlled pinch valves 23. External system interfaces are shown in FIG. 1. An internal block diagram of the major APD Cycler system components is shown in FIG. 2. The APD cycler can have a graphical user interface with pictorial guidance on proper installation orientation of the custom fitting(s) into the hardware enclosure.

Figure 3:
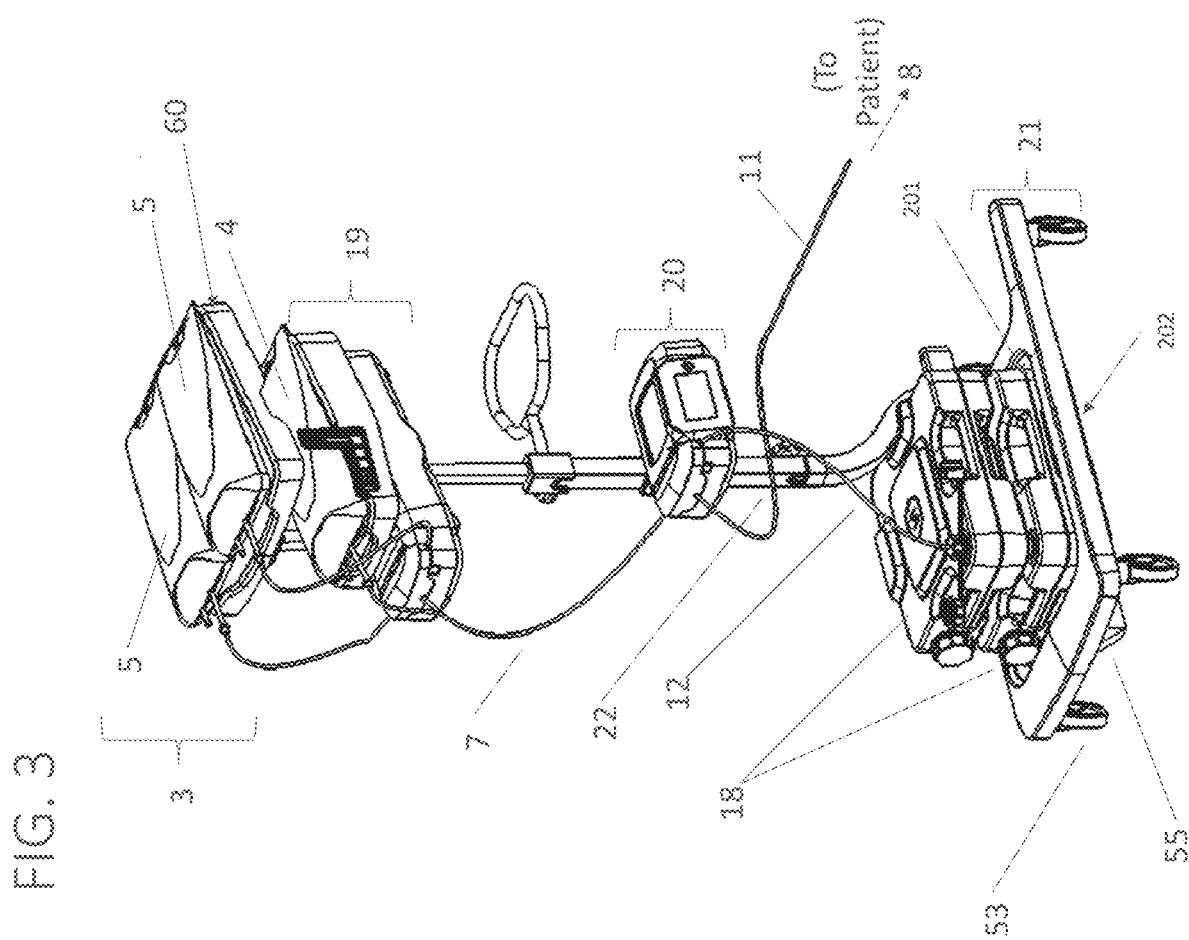
FIG. 3 illustrates the APD Pro system of the present disclosure and supports up to 3 total dialysate bags (Heater Bag, Supply Bag, and Last Fill Bag).

The system 1 can also include a disposable tubing set 7, that interfaces with the cycler's hardware pinch valves 23, the patient 8, the drain container 18, and peritoneal dialysate bags 3. This tubing set connects up to 2 off-the shelf dialysate bags (Standard) or up to 3 dialysate bags (Pro) as shown in FIG. 3. The disposable set's patient line 11 connects to the patient's 8 transfer set 10, which in turn is connected to the patient's surgically implanted peritoneal catheter 9. The disposable set's drain line 12 allows fluid to drain into the primary drain container of two reusable drain containers 18 whose collective capacity is approximately 21,000 mL (approximately 10,500 mL each). The primary drain container allows fluid to drain into the secondary drain container, either immediately, or only after the first approximately 6,000 mL has drained into the primary drain container.

Two self-closing valves, male and female, are normally closed when no therapy is in session, such as while transporting the drain containers to a tub, toilet, or sink to drain their contents. Prior to starting therapy, the self-closing valves are opened automatically by connecting the two valves together. The patient line is fitted with a disposable pinch clamp 16. The patient uses reusable removable plastic pinch clamps to shut off flow to/from the heater line 13, supply line 14, last fill line 15 (Pro only), and drain line 12. The system supports up to 18,000 mL of fresh dialysate per therapy, and up to 21,000 mL of drained dialysate in the Reusable Drain Containers 18 before the drain containers must be emptied.

The disposable tubing set can contain one or more fittings, the one leg of the solution line fitting can route fluid from a non-heated dialysate supply bag, another leg routes fluid to or from a heated dialysate bag. The optional third leg of the fitting can route fluid from a non-heated last fill dialysate bag, which is intended for delivery as a last fill bag for long daytime dwell and which may be of a different concentration or different osmotic agent than the heater bag.

In another location downstream from the solution line fitting above, a second fitting is envisioned. The one leg of the second fitting can route fluid from a heated dialysate bag, another leg routes fluid to or from a patient, and a third leg routes fluid to a drain container or drain receptacle.

FIG. 3 illustrates the peritoneal dialysis system 1, which can include hardware enclosures including, but not limited to, a Heater Unit 19, a Control Unit 20, and a Drain Unit 21. These enclosures are mounted on a Cart 22 through toolless, quick release mechanisms. Each of these components is briefly described below.

Figure 4:
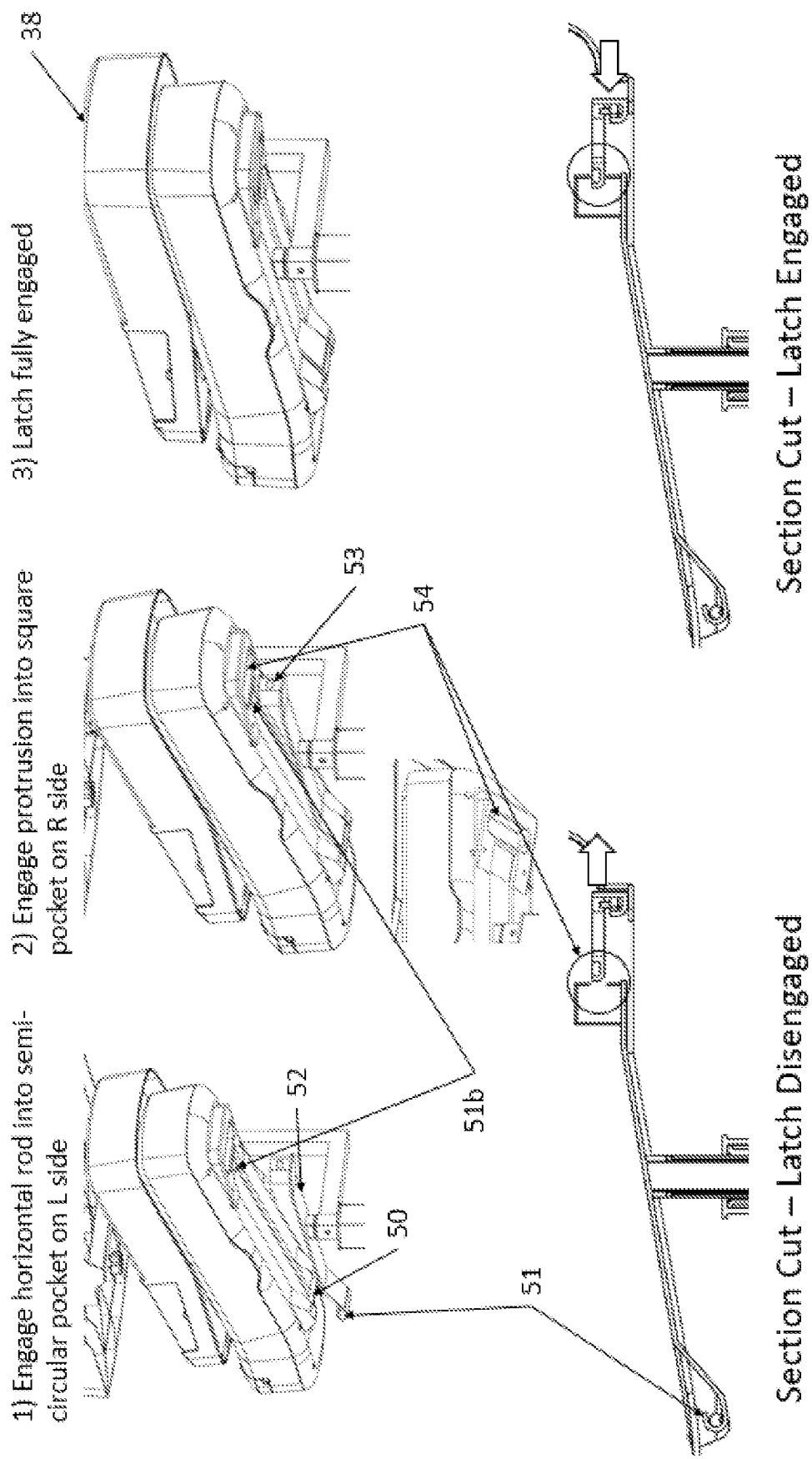
FIG. 4 illustrates a quick connect/disconnect mechanism for the Heater Unit of the APD system.

As shown in FIG. 4, the Heater Unit 19 connects to the Cart 22 by first placing the locator horizontal rod 50 on the underneath side of the heater unit into a corresponding receiver pocket 51 of the cart's top bracket 52 (similar to the back end of a typical ski boot), then pressing down on the opposite end of the heater unit such that the protrusion 53 in the cart's top bracket inserts into a pocket 51 within the heater unit and such that a spring-loaded latch 54 in the heater unit engages with a notch in the side of the protrusion 53. The Heater Unit 19 disconnects from the Cart 22 by squeezing the quick release latch 54. Neither connection nor disconnection requires any tools to actuate.

Figure 5:
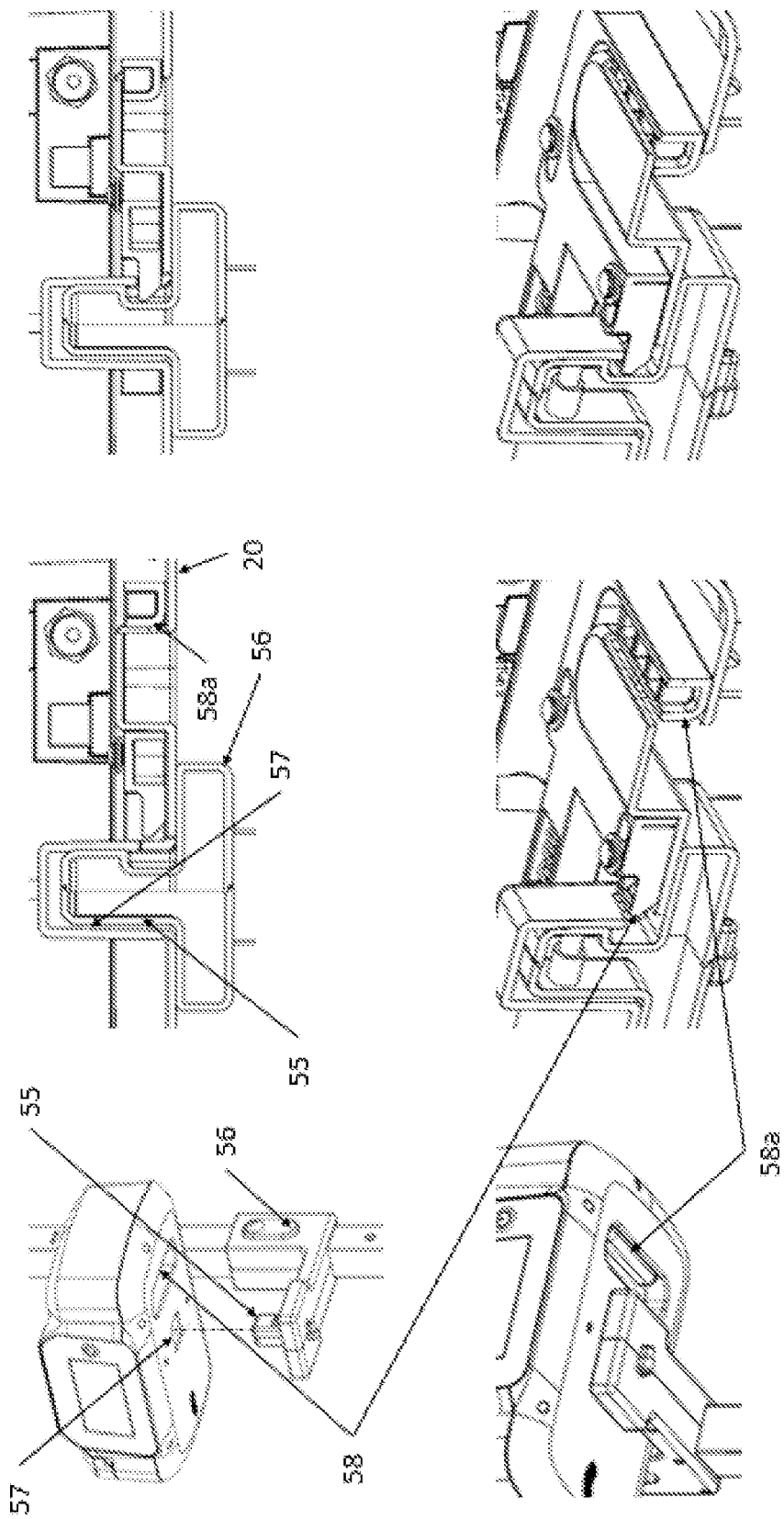
FIG. 5 illustrates a quick connect/disconnect for the Control Unit of the APD system.

As shown in FIG. 5, the Control Unit 20 connects to the Cart 22 by positioning the Control Unit above the protrusion 55 in the Middle Bracket 56 platform and pressing down on the Control Unit such that the protrusion 55 in the cart's middle bracket platform inserts into a pocket 57 within the Control Unit and such that a spring-loaded latch 58 in the Control Unit engages with a notch in the side of the protrusion 55. The Control Unit 20 disconnects from the Cart 22 by squeezing the quick release latch handle 58a. Again, neither connection nor disconnection requires any tools to actuate.

FIG. 3 illustrates a Top Shelf 60, where the supply bag and last fill bag are placed, which contains a hinge to allow the shelf to articulate out of the way so the user can more easily place the heater bag beneath the shelf without the shelf interfering. Although the top shelf 60 could have been mounted at a higher vertical distance from the heater unit to avoid interference with the heater bag, that would raise the required height at which the user must place the Supply Bag and Last Fill Bag, which may be difficult for some users.

The system can use of either one (Standard) or two (Pro) DC-powered, solenoid-driven, normally closed pinch valves 23 to control fluid delivered via the disposable tubing set to replenish either from the Supply Bag 5 to the Heater bag 4 via the Supply Replenish pinch valve 25, or the $2^{nd}$ optional Last Fill Replenish pinch valve 24 controls fluid delivered from the Last Fill Bag 6 to the Heater Bag 4 as shown in FIG. 3. A fluid flow schematic is shown in FIG. 28.

The present system 1 can use of one or more load cells 100 envisioned beneath the heater plate to weigh fluid in the Heater Bag 4, which allows the device to measure volume filled into the patient, where volume is calculated by taking into account the density of fluid delivered (V=mass/density). In one embodiment, a single highly accurate binocular beam load cell sits between the heater plate subassembly and the base of the top module enclosure. In another embodiment, up to four highly accurate load cells sit below the heater plate near each of the 4 corners. The deflection of a load cell under excessive loading conditions is very small and difficult to control. Therefore, there is a need for utilizing a load cell protection assembly to create predictable movement when excessive loading or shock loading is introduced in the dialysis system 1 of the present disclosure as described below.

Figure 8:
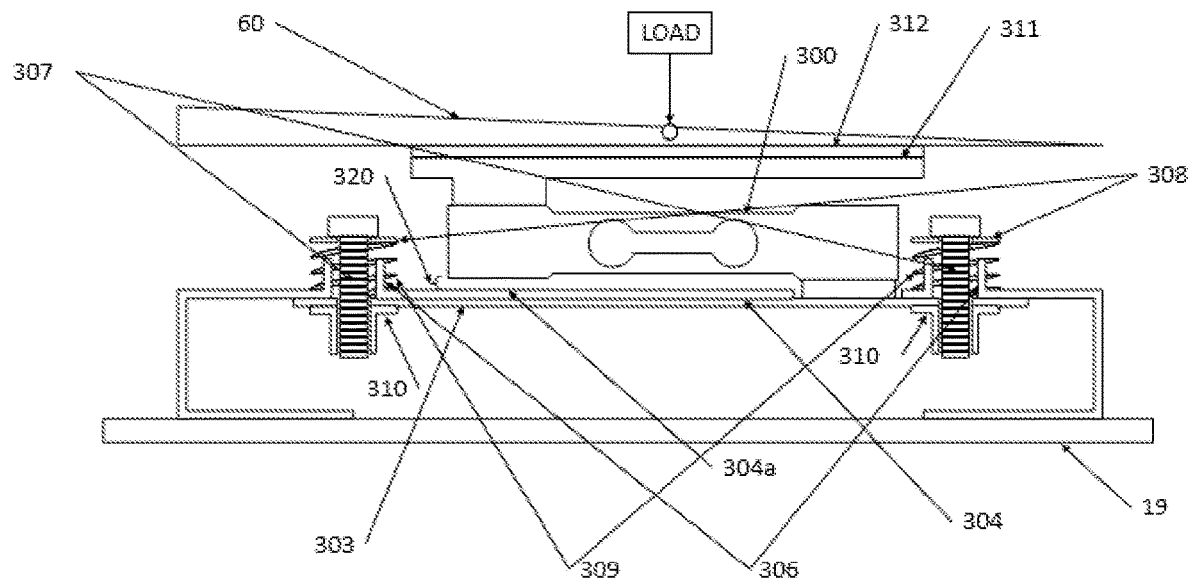
FIG. 8 illustrates an embodiment of a load cell downward protection assembly for use with a Heater Unit in the neutral position.
Figure 9:
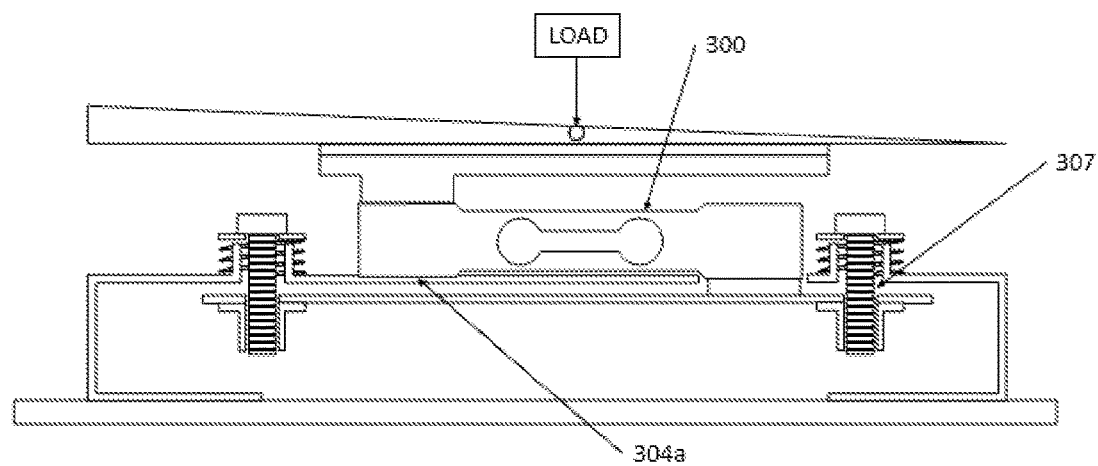
FIG. 9 illustrates the load cell downward protection assembly for use with a Heater Unit in the overload position.

As shown in FIGS. 8 and 9, the bottom of the Heater Unit load cell 300 is mounted to a Bottom Steel Plate 303. The bottom steel plate is suspended below a Base Plate 304. The Base Plate is a hat-shaped bent sheet metal with two bosses 305 welded into it, one to the left of the load cell and the other to the right, both of which are in line with the centerline of the load cell's long axis. A bushing 306 is inserted into each of the two bosses. A Down-Travel Guidepost 307, which may be a long bolt, is inserted into each of the bushings (two total). A washer 308 is placed at the top of each bolt to trap a helical compression Down-Spring 309, mounted concentric with the Down-Travel Guidepost, between the washer's lower surface and the upper surface of the Base Plate. A locking nut 310 is provided toward the bottom of the Down-Travel Guideposts 307 below the bottom surface of the Bottom Steel Plate 303.

The Down Springs 309 are preloaded by adjusting the locking nut such that the compression distance is commensurate with the spring load at or near ½ of the maximum expected normal operating load of 10 kg, since there are two Down Springs. This distance may be calculated by the spring constant formula F=Kx, where K is the spring constant and x is the compression distance. A gap 120 exists in the unloaded condition between the bottom of the left side of the load cell 300 and the Base Plate 104 (FIG. 8). Once the downward force exceeds the normal operating load of 10 kg, the load cell, Top Mounting Plate 311, and Bottom Steel Plate 303 all translate down as the springs are further compressed beyond their pre-loaded state. This ensures no translation occurs during normal loading conditions. Prior to the downward force exceeding the load cells' maximum safe overload force, the bottom of the left side of the load cell 300 rests upon the hard stop 304a, which is the top surface of the Base Plate 304 (FIG. 9). The Base Plate 304 is rigidly affixed to the Heater Unit Enclosure 19, which is itself rigidly affixed to the Cart 22 via a Quick Release Mechanism. This ensures the load cell 300 is protected from overtravel in the down direction.

Figure 10:
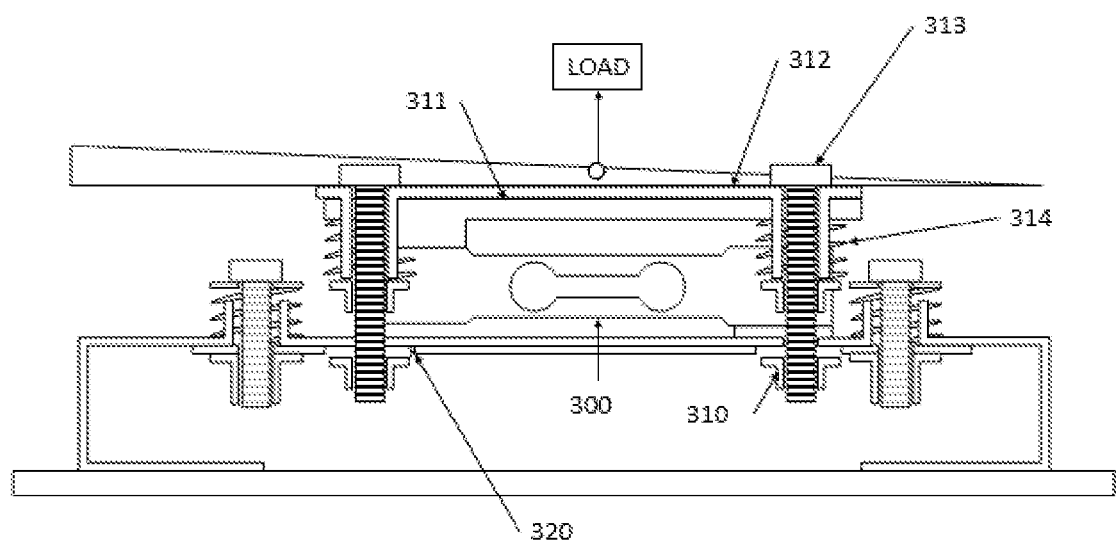
FIG. 10 illustrates an embodiment of the load cell upward protection assembly for use with a Heater Unit in the up normal load position.
Figure 11:
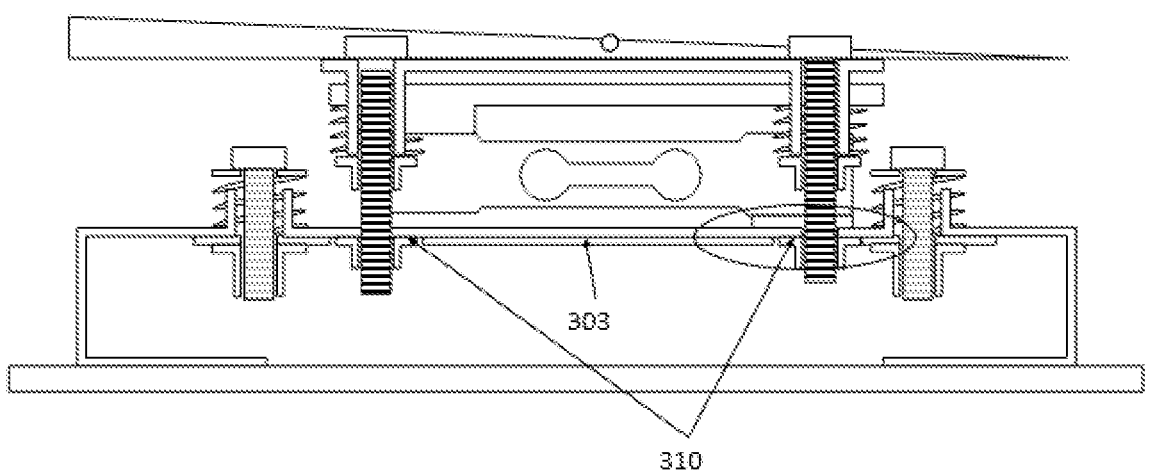
FIG. 11 illustrates the load cell upward protection assembly for use with a Heater Unit in the overload position.

As shown in FIG. 10, a plastic Top Mounting Plate 311 is mounted above the Heater Unit load cell 300. A Top Steel Plate 312 is mounted above the plastic top mounting plate, with a long screw 313 on each of the 4 corners of the top steel plate. Four helical compression Up Springs 314 are mounted concentrically around the four screws such that the top of each of the springs hits the bottom of the Top Mounting Plate 312 and the bottom of each spring hits a Locking Nut 310. The up springs 314 are preloaded by adjusting the locking nut 310 such that the compression distance is commensurate with the spring load at or near ¼ of the maximum full scale load rating of the load cell, since there are 4 Up Springs. This ensures the load cell is protected from overtravel in the up direction (FIG. 11), in which case the Locking Nuts contact the Bottom Steel Plate 303.

Figure 12:
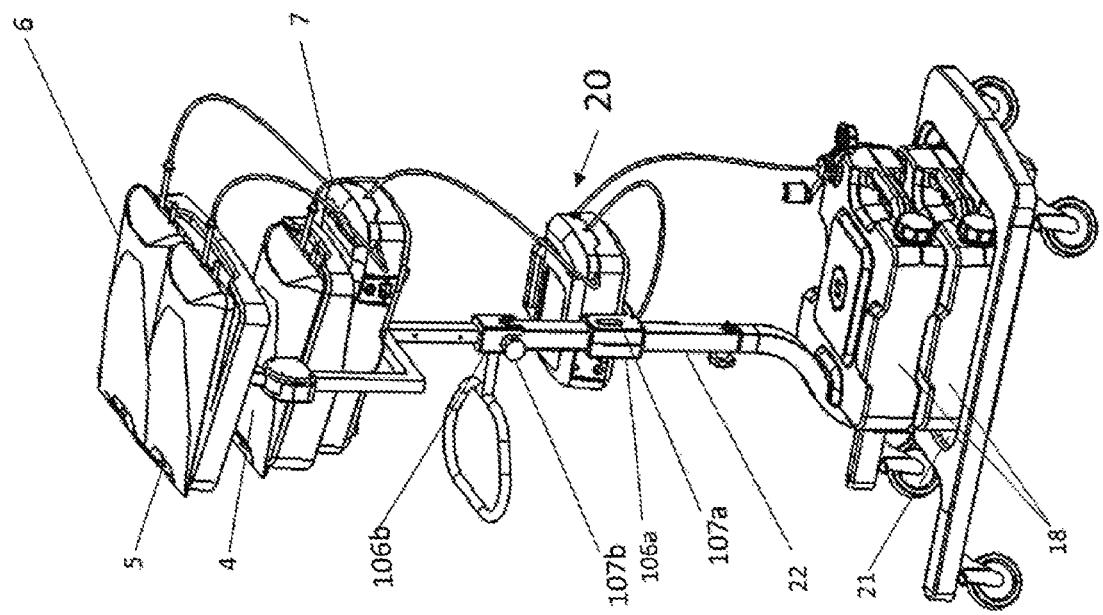
FIG. 12 illustrates another view of the APD Pro system of the present disclosure.
Figure 13:
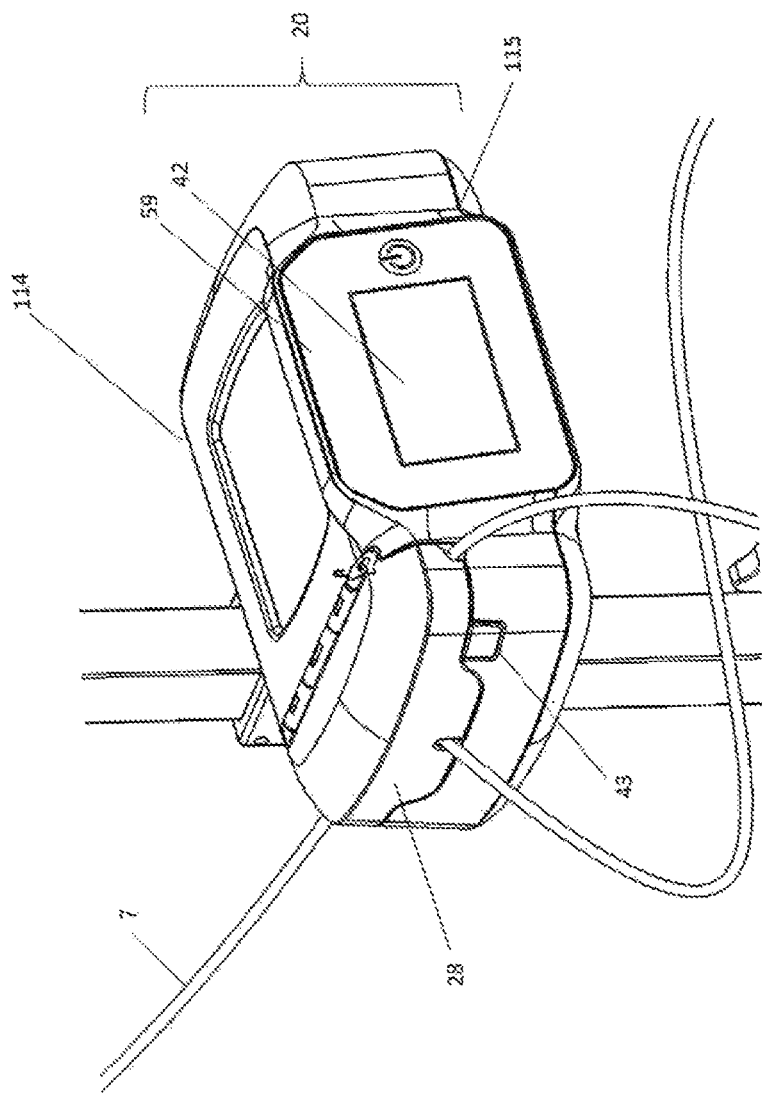
FIG. 13 illustrates the Control Unit.

As illustrated in FIGS. 12 and 13, the Control Unit 20 can be mounted on a Middle Bracket Platform 106a below the Heater Unit 19 and above the Drain Unit 21. The height of the Middle Bracket Platform is adjustable by depressing a button 107a on the side of the bracket which releases a spring-loaded pin from a hole in the side of the Pole. The Control Unit 20 can contain a color touch screen user interface 42, two pinch valves (one for filling, the other for draining the patient), a door covering the pinch valves, and a main control board with a microcontroller and associated memory for controlling system inputs and outputs. A button panel, such as a membrane panel, is included with a power button. The door can contain a latch 43 spring-loaded to the closed position via compression spring, and a hinge torsion spring to spring-load the door to the opened position. The compression spring ensures that the user must actively move the latch with a finger or thumb to the opened position so it does not inadvertently open during therapy and pose a tubing dislodgement risk and subsequent overfill/IIPV risk. The hinge torsion spring encourages the door to begin to spring open before the door latch moves back to the closed position. The Control Unit may be removed from the Pole/Bracket by squeezing a spring-loaded latch handle on the underneath side of the Control Unit, which releases a latch from a hole in the side of a square protrusion in the Bracket. A cable can connect the Heater Unit to the Control Unit, with another cable connecting the Drain Unit to the Control Unit.

The Drain Unit 21 is mounted below the Control Unit as shown in FIG. 3. The Drain Unit, measures fluid volume drained from the patient. The reusable drain container(s) 18 sit atop the Drain Unit. The Drain Unit's base plate 201 is mounted onto the base frame 202 of the Cart. The base plate 201 is used so the entire Drain Unit 21 may be assembled as a subassembly, making the necessary adjustments to the down stop gap prior to mounting the drain unit to the cart base's lower tubing structure. An alternative embodiment could involve mounting the down springs and associated bushings directly to the cart base lower tubing and omitting the base plate, in which case the cart base lower tubing would serve as the hard stop for the down stop cylinders.

Figure 14:
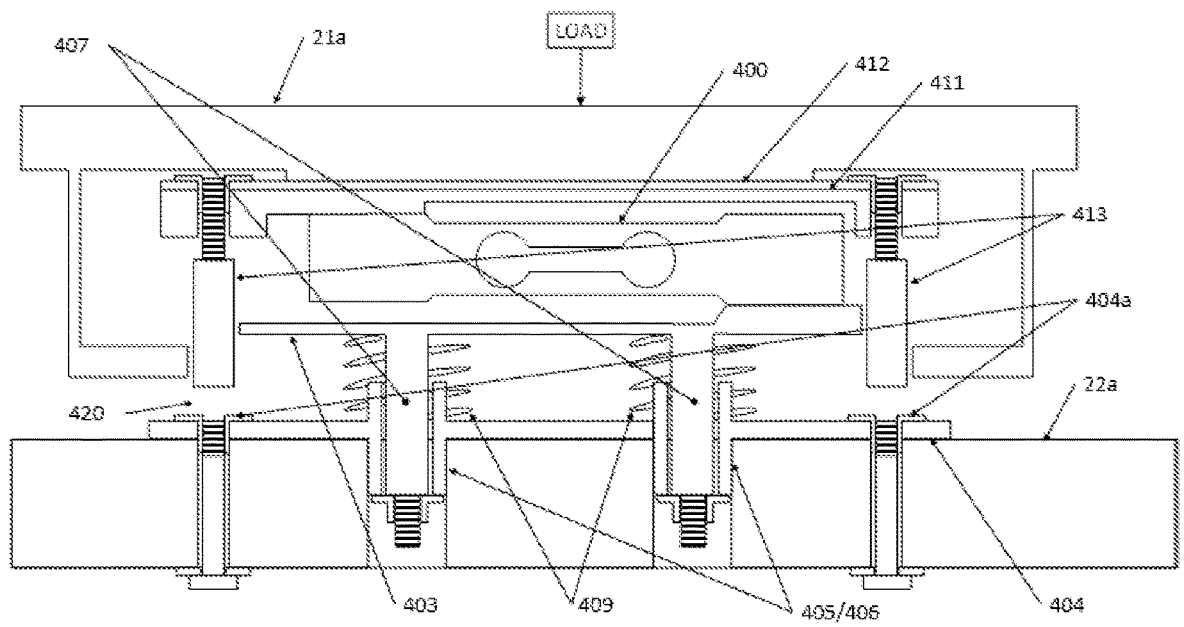
FIG. 14 illustrates an embodiment of a load cell downward protection assembly for the Drain Unit shown in the neutral position.

As shown in FIG. 14, one or more load cells 400 are envisioned beneath the Drain Unit's top surface to weigh fluid in the reusable drain container(s) 18, which allows the device to measure volume drained from the patient, where volume is calculated by taking into account the density of fluid drained (V=mass/density). In one embodiment, a single highly accurate load cell 400 sits between the Drain Unit's sides support cover and the base of the drain unit's enclosure. In another embodiment, up to four highly accurate load cells sit below the heater plate near each of the 4 corners. The load cell 400 measures the weight of fluid drained into the drain container(s) 18 during therapy and the control unit 20 uses this measurement to determine when to stop draining from the patient.

Figure 15:
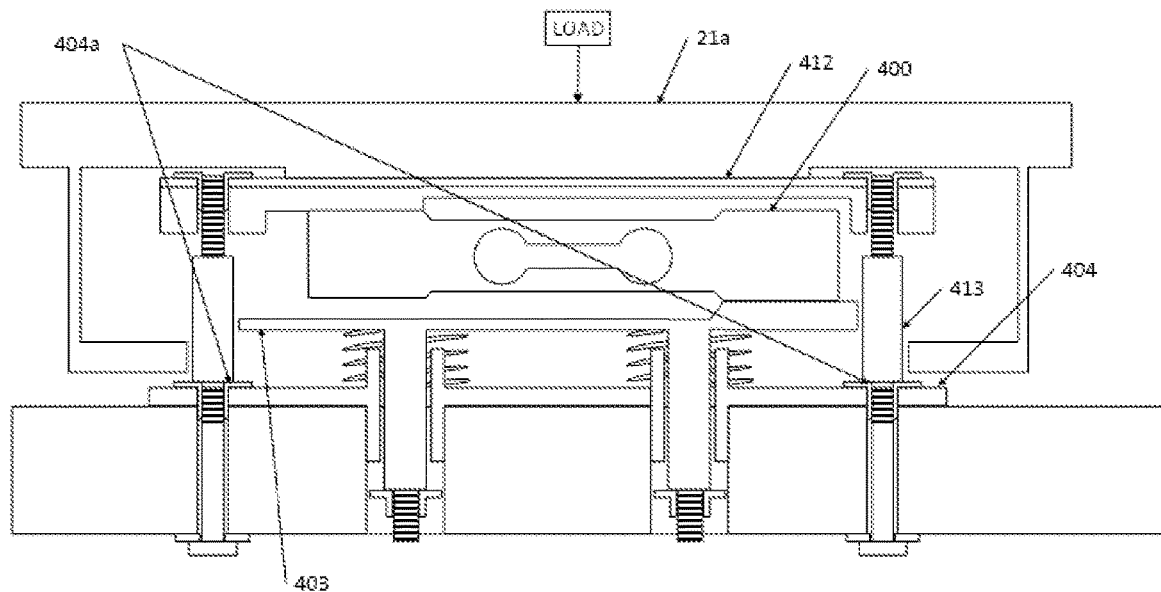
FIG. 15 illustrates the load cell downward protection assembly for the Drain Unit shown in the overload position.

As shown in FIGS. 14 and 15, the bottom of the Drain Unit load cell 400 is mounted to a Bottom Steel Plate 403. The bottom steel plate is suspended above the Base Plate 404. The Base Plate is a steel bar with two bosses 405 welded into it, one under the left side of the load cell and the other under the right, both of which are in line with the centerline of the load cell's long axis. A Bushing 406 is inserted into each of the two bosses. A pair of Down-Travel Guideposts 407 are welded to the underside of the Bottom Steel Plate, which may be long bolts, and are inserted into each of the bushings. The Bottom Steel Plate 403 traps a helical compression Down-Spring 409, mounted concentric with each of the Down-Travel Guideposts 407, between the Bottom Steel Plate's lower surface and the upper surface of the Base Plate. A locking nut 410 is provided toward the bottom of each Down-Travel Guidepost 407 below the bottom surface of the Bottom Steel Plate. The Down Springs 409 are preloaded by adjusting the locking nut such that the compression distance is commensurate with the spring load at or near ½ of the maximum expected normal operating load range of 20-50 kg, since there are two Down Springs. This distance may be calculated by the spring constant formula F=Kx, where K is the spring constant and x is the compression distance. A plastic Top Mounting Plate 411 is mounted above the Drain Unit load cell 400.

A Top Steel Plate 412 is mounted above the plastic top mounting plate. A pair of down stop cylinders 413, which may be bolts, are screwed into the bottom of the Top Steel Plate, one to the left of the load cell 400 and the other to the right. A gap 420 exists in the unloaded condition between the bottom of each of the Down Stop Cylinders 413 and the top of the Base Plate. Once the downward force exceeds the normal operating load of 30 kg, the load cell 400, Top Mounting Plate 411, Top Steel Plate 412, Drain Container Tray 201a, and Bottom Steel Plate 403 all translate down as the springs are further compressed beyond their pre-loaded state (FIG. 15). This ensures no translation occurs during normal loading conditions. Prior to the downward force exceeding the load cells' maximum safe overload force, the bottom of the left and right Down Stop Cylinders 413 rest upon the hard stops 404a, which are the top surface of the Base Plate 404. The Base Plate is rigidly affixed to the Cart base lower tubing 22a, which is itself welded to the rest of the Cart Base 202. This ensures the load cell 200 is protected from overtravel in the down direction.

Figure 16:
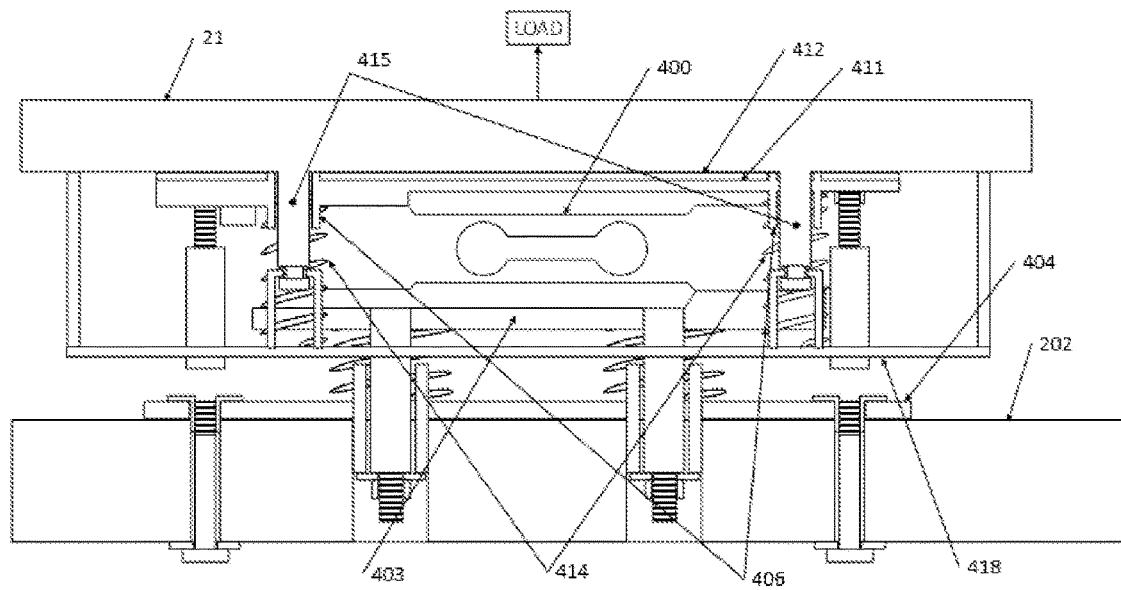
FIG. 16 illustrates an embodiment of a load cell upward protection assembly for the Drain Unit shown in the neutral position.
Figure 17:
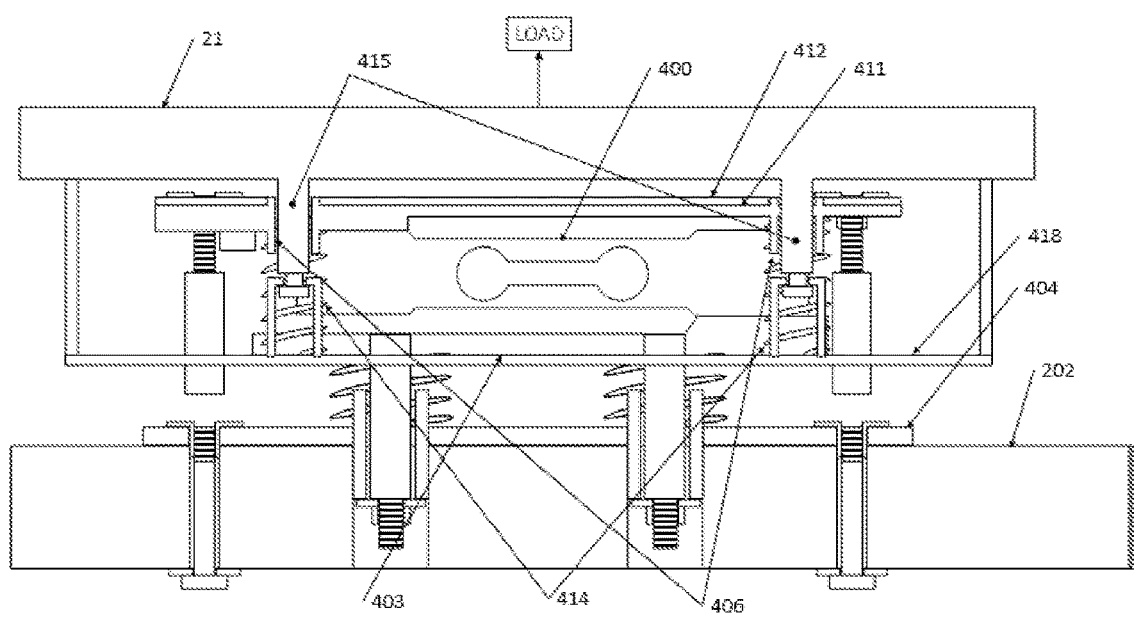
FIG. 17 illustrates the load cell upward protection assembly for the Drain Unit shown in the overload position.

As shown in FIGS. 16 and 17, the Top Steel Plate 412 above the load cell 400 has a long screw on each of the 4 corners. Four helical compression Up Springs 414 are mounted concentrically around the four screws such that the top of each of the springs hits the bottom of the Top Mounting Plate 411 and the bottom of each spring hits the bottom cover 218. The up springs are preloaded by adjusting a screw in each of four Up Travel Guideposts 415 such that the compression distance is commensurate with the spring load at or near ¼ of the maximum full scale load rating of the load cell, since there are four Up Springs 414. At or before reaching the maximum full scale load rating, the top of the bottom cover 418 rests on the bottom of the bottom steel plate. This ensures the load cell is protected from overtravel in the up direction (FIG. 17).

Figure 18:
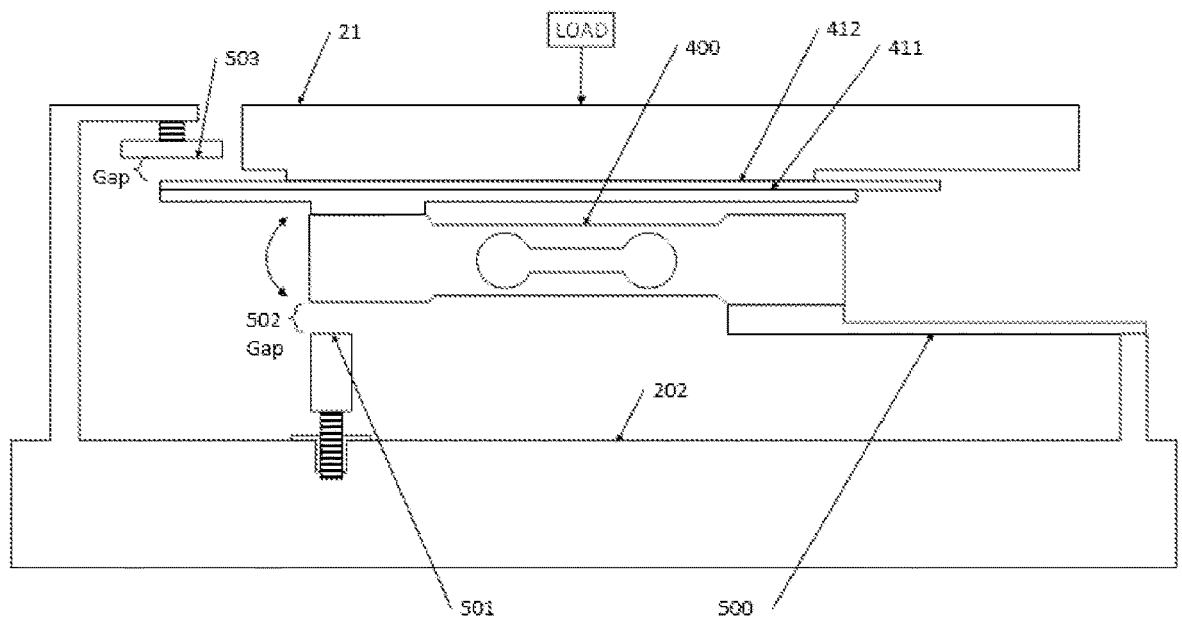
FIG. 18 illustrates an alternative embodiment of a load cell protection assembly utilizing a flat spring for the Drain Unit shown in the neutral position.
Figure 19:
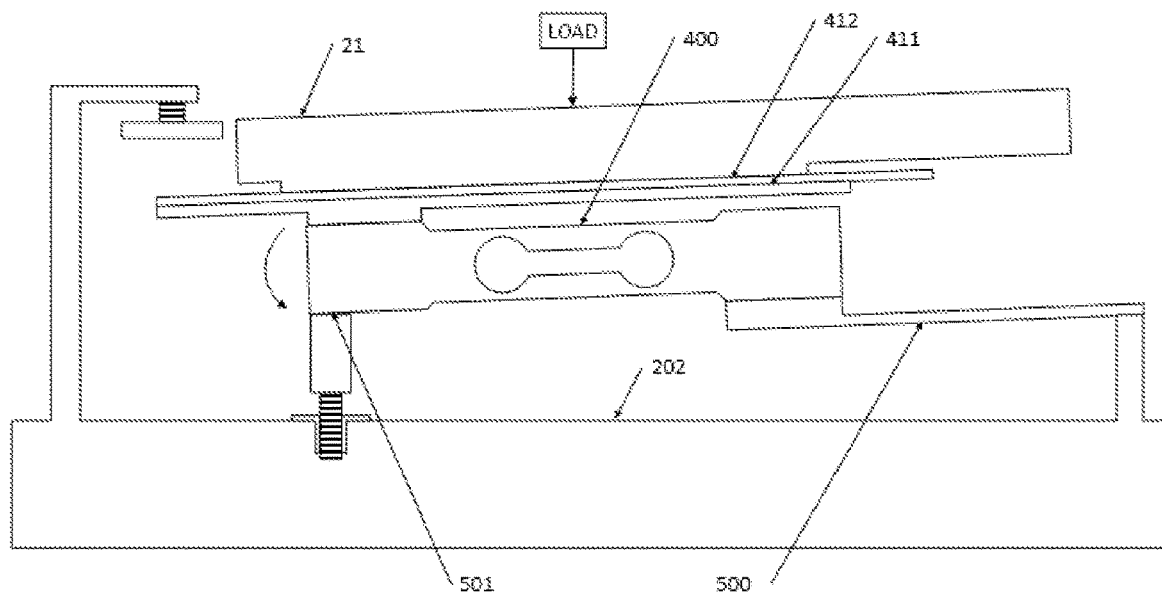
FIG. 19 illustrates the alternative embodiment of a load cell protection assembly utilizing a flat spring for the Drain Unit shown in the downward overload position.
Figure 20:
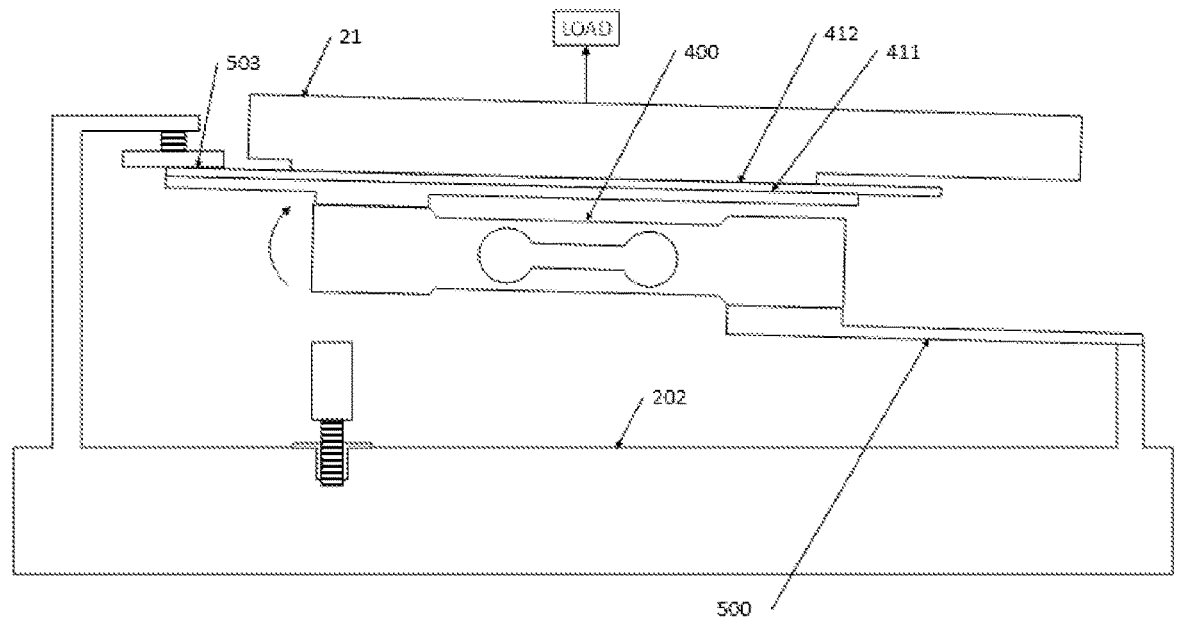
FIG. 20 illustrates an alternative embodiment of a load cell protection assembly utilizing a flat spring for the Drain Unit shown in the upward overload position.
Figure 21:
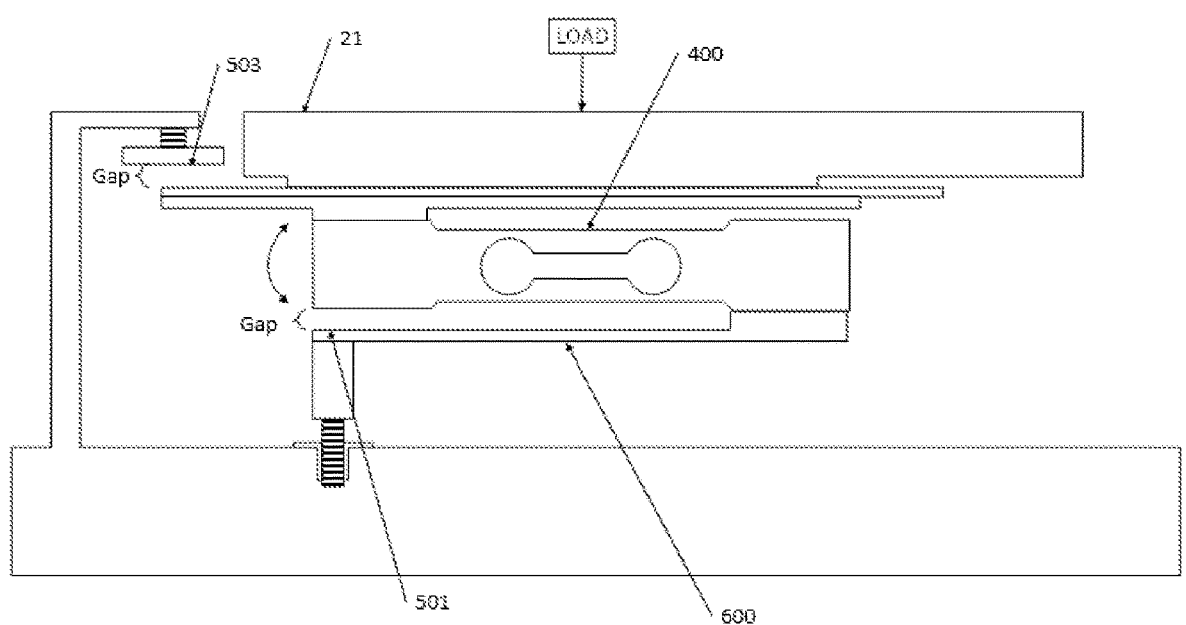
FIG. 21 illustrates yet another alternative embodiment of a load cell protection assembly utilizing a flat spring beneath a load cell for the Drain Unit shown in the neutral position.
Figure 22:
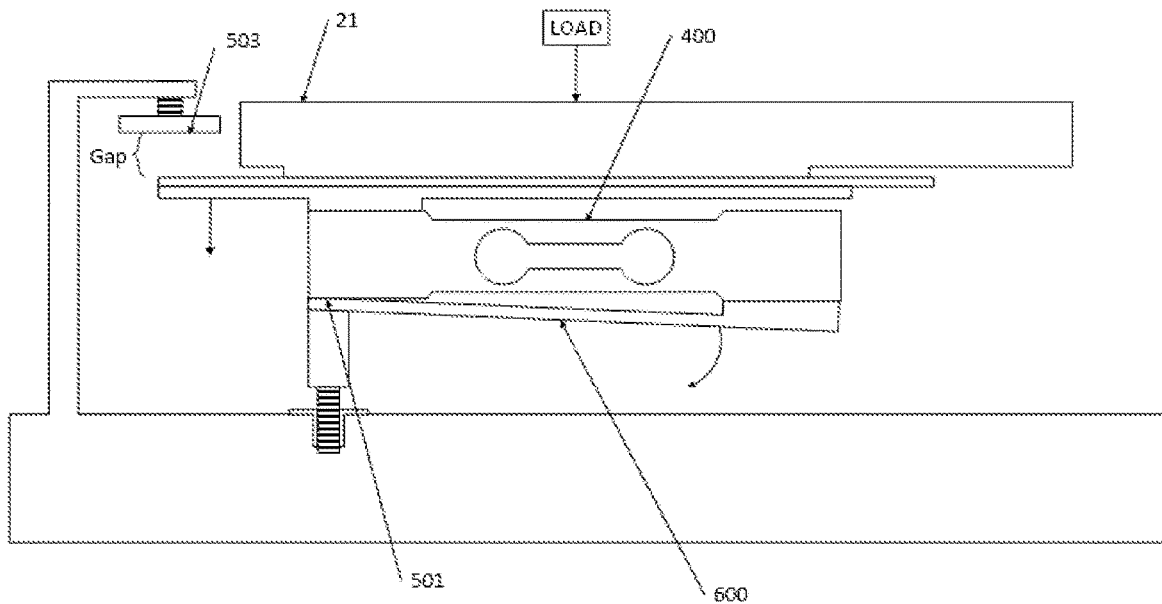
FIG. 22 illustrates yet another alternative embodiment of the load cell protection assembly utilizing a flat spring beneath a load cell for the Drain Unit shown in the downward overload position.
Figure 23:
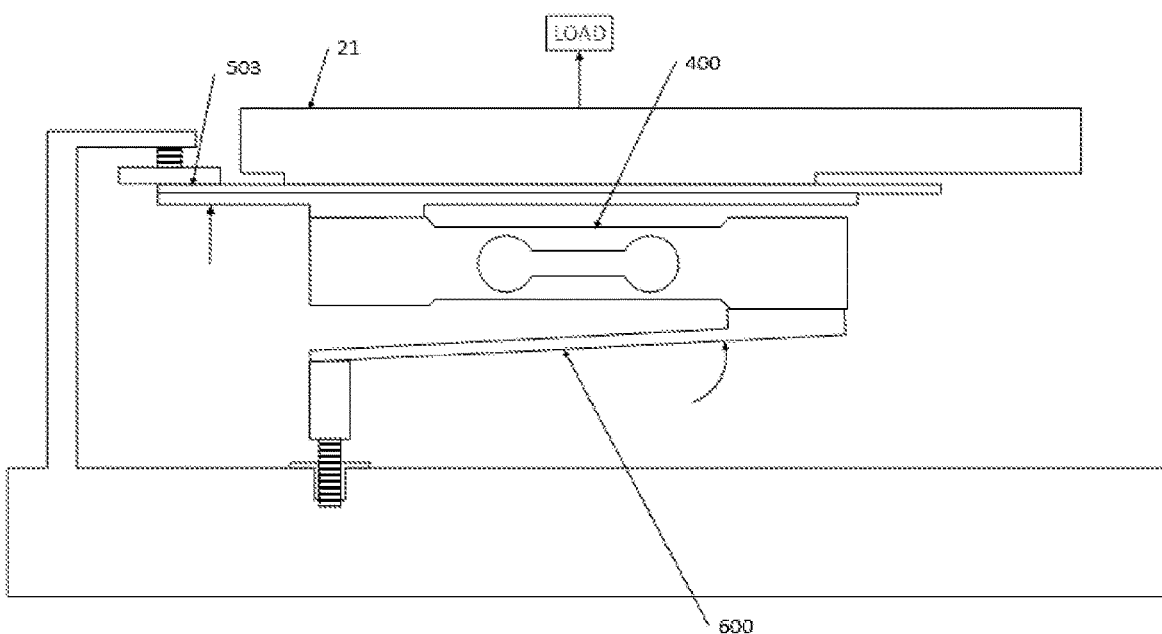
FIG. 23 illustrates yet another alternative embodiment of a load cell protection assembly utilizing a flat spring beneath a load cell for the Drain Unit shown in the upward overload position.

FIGS. 18-23 show alternative embodiments of overload protection assemblies for use with the load cell. These embodiments show a single flat spring 500 mounted beneath the load cell 400 such that the load cell travels further with an applied load than it would without the flat spring. In FIGS. 18-20, this flat spring could be mounted such that the load cell extends off the edge of it as if extending off the edge of a diving board, or the spring could be mounted such that the lower mounting point of the flat spring is approximately directly below the upper mounting point of the load cell where it meets the platform being weighed, similar to a Z-shape as shown in FIGS. 21-23. In this manner, the total system is more compact and has less total vertical travel at the point of the platform furthest away from the load cell mounting point.

As shown in FIG. 18, with the flat spring configuration, a down stop 501 may be located directly underneath the load cell 400. In the unloaded configuration, a gap 502 exists between the load cell and the down stop. At or before reaching the maximum safe overload force, the bottom of the load cell touches the down stop (FIG. 19). The down stop 501 need not be located directly under the load cell, nor does the load cell need to serve as the object striking the down stop, but rather, the down stop may be located under any other structure that moves with the load cell, which could include a plate above or below the load cell.

With the flat spring configuration, an optional up stop 503 may be located above the top steel plate mounted above the load cell. In the unloaded configuration (FIG. 18), a gap exists between the bottom surface of the up stop and the top surface of the top steel plate. As shown in FIG. 20, the top steel plate hits the up hard stop at or before the load reaches the load cell's maximum overtravel limit force.

FIGS. 21-23 show yet another embodiment with the flat spring 600 positioned completely underneath the load cell 400. In this embodiment, the movement is primarily vertically up and down rather than rotating significantly.

In an embodiment shown in FIG. 3, the Cart 22 is vertical pole with a lower S-section and a wheeled base. The Drain Unit 21 is permanently mounted to the base of the Cart. The Heater Unit and Control Unit mount to the Cart via quick disconnect mechanisms using a spring-loaded latch which is squeezed by the user to release the latch and allow for vertical height adjustment of the Heater Unit or Control Unit along the pole, as previously described. In this embodiment, the Cart has 4 casters 53 on its base 55 and a Top Shelf 60 holding one or two bags 5 at the top of the pole. The pole is constructed of steel square tubing. The pole must be capable of allowing the Heater Unit to extend to a height which falls within the range of 48" to 56" from the ground.

The Cart can be integrated with the Drain Unit 21, as shown in FIG. 3. In this embodiment, there are four caster wheels 53. The casters are rotatable in 360° and may be locking-type. The vertical structure consists of one S-shaped square tube with a concentric smaller diameter square tube at the top that affixed to the base, along with one straight square tube of the same outer diameter that mounts to the top of the S-shaped share tube. A smaller diameter straight square tube is mounted within the larger diameter straight square tube. This smaller diameter tube has a lower L-bracket welded to the side at the top of the smaller tube. At the top of the L-bracket, a spring-loaded hinge connects the lower L-bracket to an upper L-bracket. A Top Shelf is mounted to the upper L-bracket via finger knobs for ease of disassembly for travel. Both the smaller and larger diameter straight square tubes are perforated at regular intervals along the vertical axis to provide for variable height adjustment of the Heater Unit 19 and/or Control Unit 20. Adjustable Heater Unit heights allow shorter patients the ability to place the Heater Bag 4 onto the Heater Unit at a lower height, and allow patients needing greater Fill flow rates to achieve them by raising the Heater Unit. The Control Unit's adjustability allows patients to keep the Control Unit's display 42 and button panel 59 easily accessible for sleeping patients whose bed heights may differ from each other.

The Heater Unit, Control Unit, S-pole, Larger OD straight pole, Smaller OD straight pole, and Top Shelf may be detached from the Cart Base to facilitate portability for travel. It may also facilitate different APD device configurations by swapping out certain components or subsystems, while maintaining other components or subsystems, with each component or subsystem mounted to the Cart. In one embodiment, this may include an optional push/pull handle to push or pull the entire pole and attached APD system within the home. In this manner, multiple region-specific APD device configurations may be envisioned. Additionally, one or more optional components or subsystems may be added to the APD device by clamping additional components or subsystems to the Cart's pole. This may include a component or subsystem 61 intended to assist in lifting dialysate bags to the proper height. The casters may be detachable from the base to further facilitate portability for travel.

In one embodiment, shown in FIG. 12 the enclosure detachment mechanism is a spring-loaded latch mounted inside of one or more of the Heater Unit and Control Unit, each of which mates with a platform shelf bracket which attach to the square tubing via a pin 107 placed into one of the perforated holes. The pin could be spring-loaded into the hole.

By utilizing a vertical structure, whereby the Heater Unit and Control Unit, are affixed to the vertical pole and the Drain Unit is affixed to the Cart Base, this offers advantages over traditional active pumping APD devices. Traditional APD devices typically have the Heater Bag mounted atop the device, with the Supply Bag(s) and Last Fill Bag situated next to the device. This requires the patient to have a large nightstand, table, or large cart to place all of these items, with a correspondingly large footprint on the patient's floor and little to no portability within the home. The vertical structure takes up less footprint on the floor. Additionally, with the inclusion of wheels in the pole's design, the system is more portable within the patient's home (or hospital) than traditional active pumping APD devices.

Figure 25:
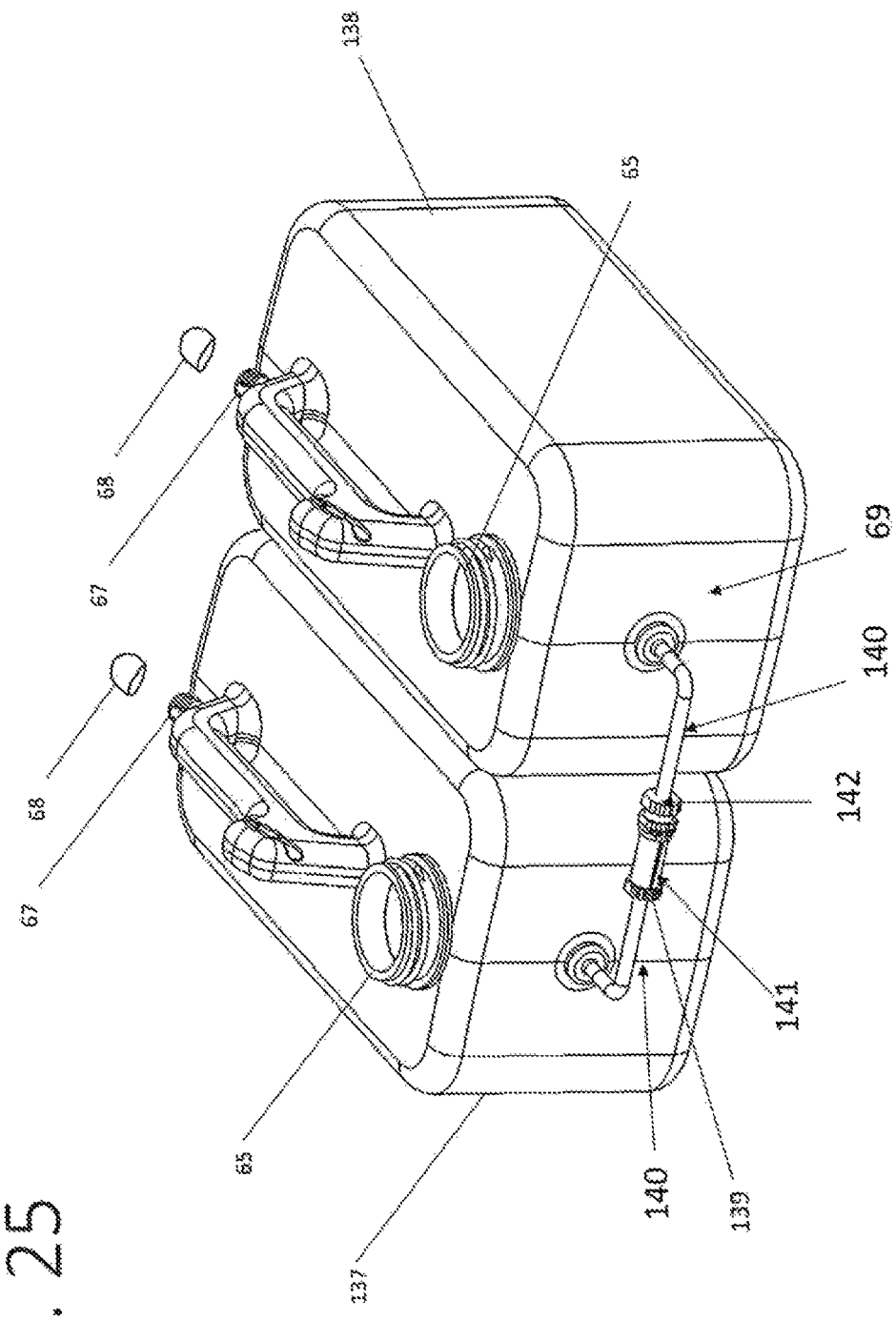
FIG. 25 illustrates a side-by-side configuration of reusable drain containers.
Figure 26:
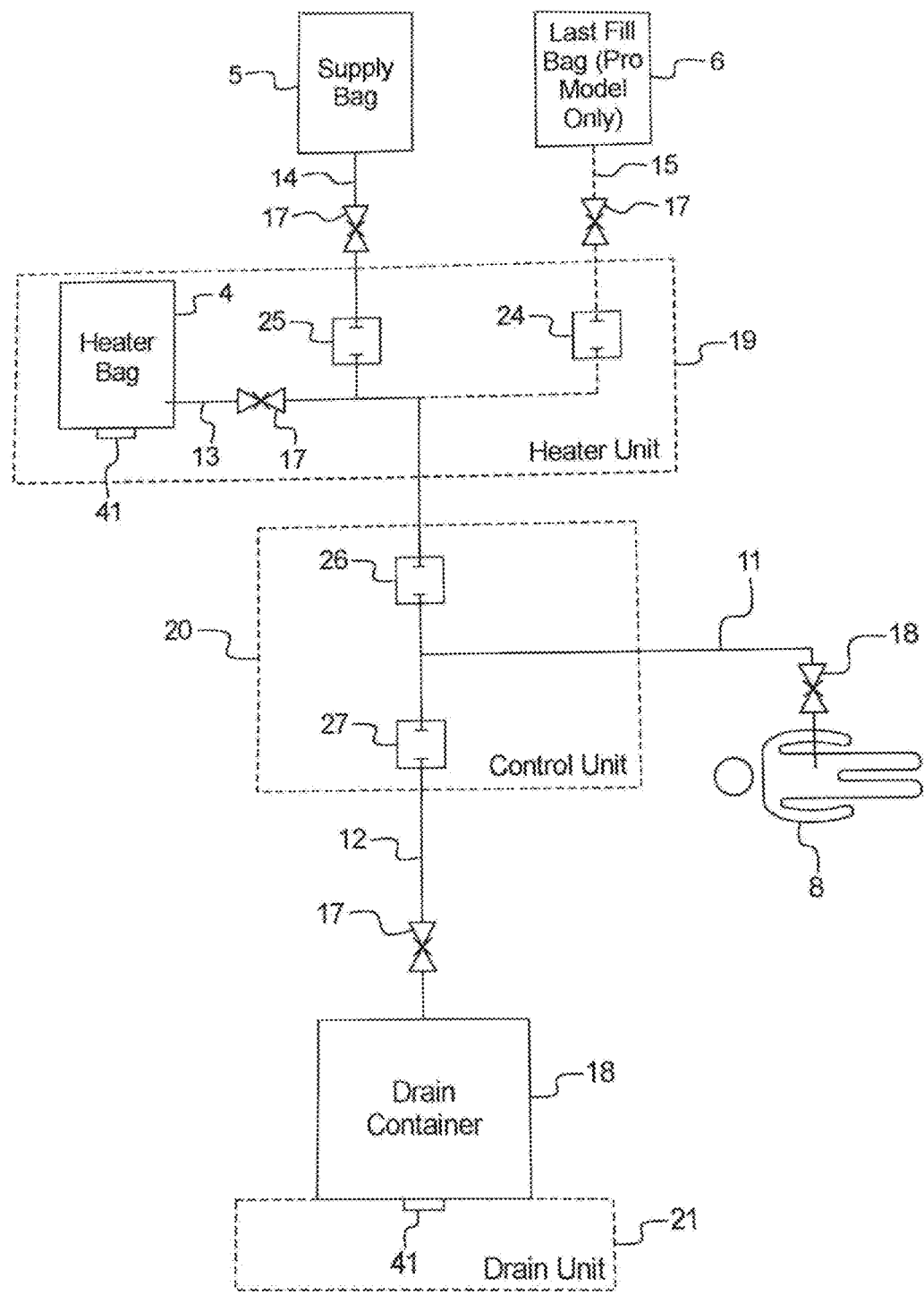
FIG. 26 illustrates a fluid flow schematic for the APD system.

As mentioned, the present peritoneal dialysis system 1 can include a pair of reusable drain containers 18 that sit atop the Drain Unit 21 as shown in FIG. 3. The drain containers 18 to serve as a 15,000-21,000 mL reservoir for spent effluent drained from the patient. The drain container 18 or containers, in one embodiment, is transparent to allow the user to view the cloudiness of the spent effluent, which is a sign of potential peritonitis. A drain line clip integrates with the drain container to ensure an air gap is maintained between the disposable tubing set's drain line 12 and the maximum fluid level within the drain container. By offering reusable drain containers, this system saves cost over traditional APD devices which offer a single-use disposable drain container. Each reusable drain container contains a large spout 65 for pouring the contents into a floor drain, toilet, or tub. A removable spigot with integrated valve may be placed over the spout via threaded connection via base. This spigot allows the user to open the valve and leave the drain container draining (e.g. into a floor drain) while the user is able to walk away without continuously holding it and waiting for it to complete. A vent hole 67 and associated cap 68 is included on the opposite side from the spout to reduce sloshing while emptying the contents of the drain container (FIG. 25). The drain container, in one embodiment, has a flat side 69 (FIG. 24-25) to allow the user to leave it on a toilet seat or floor drain in a tipped up configuration for the entire contents of its fluid to flow out the spout or spigot, again, allowing the user to walk away without holding it continuously to wait for it to complete.

As shown in FIGS. 24 and 25, the present peritoneal dialysis system 1 can utilize an effluent drain receptacle that is split into two smaller reusable drain containers, a primary 137 and a secondary 138, each with a capacity of approximately half of the total system's drain capacity, which equates to approximately 7,500 to 10,500 mL each. The two drain containers can sit side-by-side on the drain unit 21 (FIG. 25). Alternatively, they could be arranged with the primary container 137 in a stackable shape, and the secondary container 138 resting beneath the primary container, or vice versa (FIG. 24). In either configuration, fluid from the disposable tubing set's drain line 12 flows into the primary container (FIG. 3).

As shown in FIG. 25, the primary drain container 137 contains an outflow valve 139 which, when the container is full or partially full, begins delivering fluid to the secondary drain container 138 as additional fluid is drained from the patient. The secondary container's inlet valve 65 mates with the primary container's outlet valve 139 such that it receives overflow fluid from the primary container. A cap may be placed over the containers' respective outflow valve and/or the spout for transport and storage. Each of the primary and secondary containers may also have a vent hole on the opposite side from the spout to prevent an internal vacuum while emptying the contents from the spout into a tub, toilet, or floor drain. This embodiment has the advantage of ensuring the user does not have to lift the entire weight of a single 15,000 to 21,000 mL drain container, but only has to lift approximately half that weight at any given time. Of course, any number of drain units can be used. For example, the system may have 3 or more drain containers with overflow fluid passing from one to the next to the next, rather than the two drain containers described herein.

As shown in FIG. 25, in the side-by-side drain container configuration, the user places the primary drain container 137 next to the secondary drain container 138, both of which rest on the Drain Unit platform, which is keyed to prevent improper orientation. A tube 140 exits the side of each drain container, one of which terminates in a normally closed male quick disconnect 141, and the other terminates in a normally closed female quick disconnect 142. The user connects the male and female quick disconnects. Once engaged, both valves will open to allow fluid to flow from the primary drain container to the secondary drain container. The height of the tube exiting the primary drain container may be such that the fluid level does not reach the tube until approximately 6000 mL have been filled into the primary drain container. Once this fluid level is reached, as more fluid enters the primary drain container from the disposable tubing set's drain line, which drains fluid from the patient via the patient line, the secondary drain container begins filling until it reaches the same fluid level as the primary drain container. As the secondary drain container fills, it purges its air through vent holes in the top of the drain container. Once both drain containers are full or close to full, each will contain approximately 10,500 mL.

In FIG. 24, in particular 24a showing the stackable drain container configuration and 24b showing the exploded version of the stackable drain containers, the user places the primary drain container 137 on top of the secondary drain container 138, which rests on the Drain Unit platform 21, which is keyed to prevent improper orientation. In doing so, a valve 139 on the bottom side of the primary drain container 137 which is normally spring-loaded closed will engage with another valve on the top side of the secondary drain container 138, which is also normally spring-loaded closed, and once engaged, both valves will open to allow fluid to flow from the primary drain container to the secondary drain container. The height of the outflow valve in the primary drain container is such that the fluid level does not reach the valve's outlet port until approximately 6000 mL have been filled into the primary drain container. Once this fluid level is reached, as more fluid enters the primary drain container from the disposable tubing set's drain line, which drains fluid from the patient via the patient line, the secondary drain container begins filling until it is full. As the secondary drain container fills, it purges its air through vent holes in the valves until the air reaches the primary drain container and exits out the primary drain container's spout. Once the secondary drain container is completely full, additional fluid will then continue filling the primary drain container until both drain containers are full or close to full, each containing approximately 10,500 mL.

Figure 6:
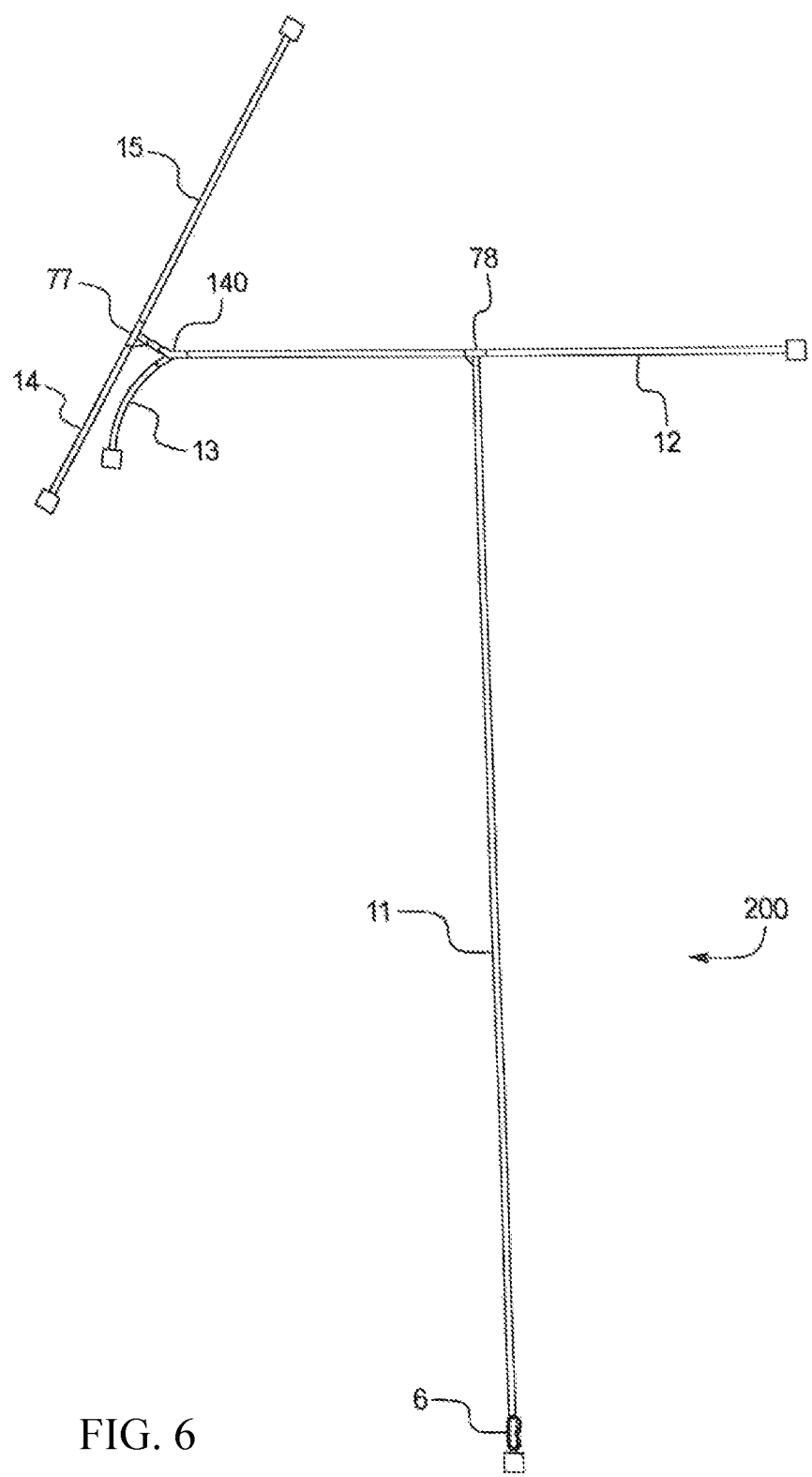
FIG. 6 illustrates the Pro model disposable tubing set with the extra tubing line and associated connector for connecting to a unique Last Fill Bag.
Figure 7:
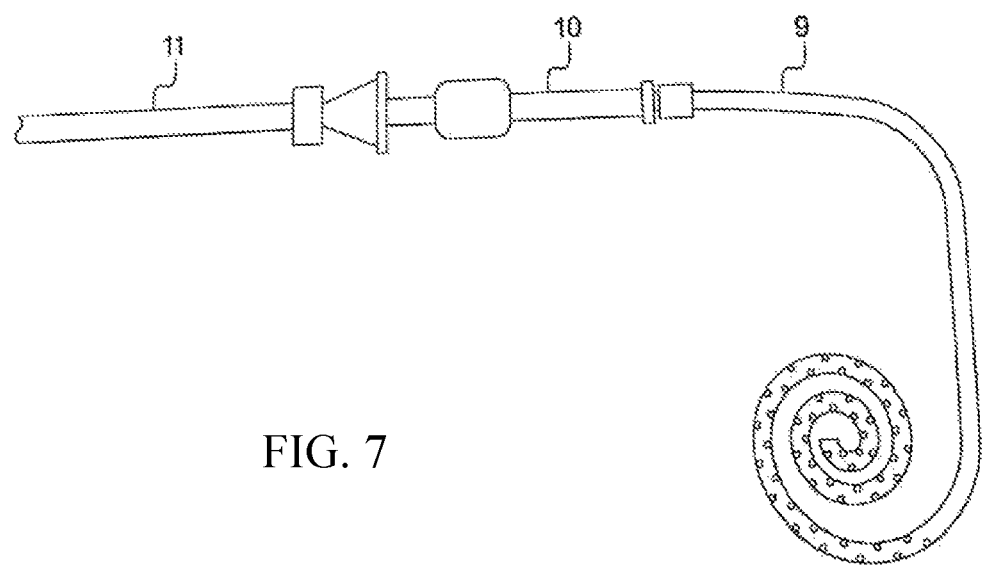
FIG. 7 illustrates how the proposed disposable tubing set (Standard or Pro) connects to a transfer set, which in turn connects to the patient's surgically implanted PD catheter.

The present peritoneal dialysis system 1 can include a sterile, single-use disposable tubing set 200, as shown in FIG. 6, and its associated hardware interfaces. The proposed disposable set consists of medical-grade, biocompatible PVC tubing, a patient line tubing clamp, and molded plastic connectors with caps. Reusable clamps can be used for all tubing lines except the patient line, which has a disposable clamp integrated into the tubing set. Sets are available with multiple bag connector fitting types for interfacing to various off-the-shelf peritoneal dialysate bags. The internal contents of the tubing set are sterilized. Each tubing set can be packaged in a poly pouch, several of which are packaged together in a cardboard box for shipping and distribution.

As illustrated in FIG. 6, the Standard model tubing set can contain a Heater Line 13 tube and associated connector for connecting to a Heater Bag. The tubing set can include a Supply Line 14 tube, associated connector for connecting to a Supply Bag, a Drain Line 12 tube for connecting to the Drain Container, and a Patient Line 11 tube and associated connector for connecting to the patient's catheter or catheter transfer set. Unlike conventional APD tubing sets, the present system includes a tubing set which does not contain a cassette, since fluid flow is controlled via electronically controlled, solenoid-operated pinch valves and gravity provides the motive force for fluid delivery. All lines and/or connectors with exposed fluid paths are fitted with vented caps to maintain sterility and facilitate ethylene oxide sterilization.

In an example, the disposable set for the Pro model is identical to that of the Standard except it contains one extra tubing line and associated connector to connect to the Last Fill solution bag 6. Both tubing set configurations may have one or more optional Y-fittings or manifolds to connect additional Supply Bag. The system can include solution line connectors for connecting the Supply Bag, Heater Bag, and optional Last Fill Bag, which are designed to reduce the likelihood of peritonitis due to touch contamination.

As shown in FIG. 6, an additional wye fitting 140 can connect the Heater Line 13 to the tubing headed toward the Control Unit, with the third leg of the wye connecting to a short tube whose opposite end connects to Fitting #1. This allows either the Supply Bag or Last Fill Bag to replenish the Heater Bag by opening either the Supply Valve or Last Fill Valve.

As shown in FIGS. 28 and 29, the APD device can include three (Standard) or four (Pro) spring-loaded, normally closed solenoid-operated pinch valves 23 to control fluid delivery from source dialysate containers to the patient, and from the patient to the drain destination. Normally closed pinch valves offer benefits to prevent unintended Increased Intraperitoneal Volume (IIPV)/overfill, or unintended draining in the event of loss of power to the pinch valves (fail safe).

This device envisions one normally closed pinch valve 25 to control fluid replenishment from one or more Supply dialysate bags 5 to a Heater dialysate bag 4.

Another optional last fill pinch valve 24 is envisioned for the Pro model to control fluid replenishment from a Last Fill dialysate bag 6, such as icodextrin, to the Heater bag 4. One device configuration (Standard model) may omit the Last Fill valve for patients who use the same dextrose-based fluids for their Last Fill as their other Fill phases and do not require a unique fluid type such as icodextrin for their Last Fill. The Last Fill fluid remains in the patient's abdomen for the long daytime dwell period. Another Patient Fill pinch valve 26 can be included for filling the patient, controlling fluid flow from the Heater Bag 4 which sits on a heated surface 38, to the patient 8. The patient's peritoneal catheter remains below the heater bag for gravity flow.

As mentioned above, aspects of the systems and methods described herein are controlled by one or more controllers. The one or more controllers may be adapted to run a variety of application programs, access and store data, including accessing and storing data in the associated databases, and enable one or more interactions as described herein. Typically, the controller is implemented by one or more programmable data processing devices. The hardware elements, operating systems, and programming languages of such devices are conventional in nature, and it is presumed that those skilled in the art are adequately familiar therewith.

For example, the one or more controllers may be a PC based implementation of a central control processing system utilizing a central processing unit (CPU), memory and an interconnect bus. The CPU may contain a single microprocessor, or it may contain a plurality of microprocessors for configuring the CPU as a multi-processor system. The memory may include a main memory, such as a dynamic random access memory (DRAM) and cache, as well as a read only memory, such as a PROM, EPROM, FLASH-EPROM, or the like. The system may also include any form of volatile or non-volatile memory. In operation, the memory stores at least portions of instructions for execution by the CPU and data for processing in accord with the executed instructions.

The one or more controllers may also include one or more input/output interfaces for communications with one or more processing systems. Although not shown, one or more such interfaces may enable communications via a network, e.g., to enable sending and receiving instructions electronically. The communication links may be wired or wireless.

The one or more controllers may further include appropriate input/output ports for interconnection with one or more output mechanisms (e.g., monitors, printers, touchscreens, motion-sensing input devices, etc.) and one or more input mechanisms (e.g., keyboards, mice, voice, touchscreens, bioelectric devices, magnetic readers, RFID readers, barcode readers, motion-sensing input devices, etc.) serving as one or more user interfaces for the controller. For example, the one or more controllers may include a graphics subsystem to drive the output mechanism. The links of the peripherals to the system may be wired connections or use wireless communications.

Although summarized above as a PC-type implementation, those skilled in the art will recognize that the one or more controllers also encompasses systems such as host computers, servers, workstations, network terminals, and the like. Further one or more controllers may be embodied in a device, such as a mobile electronic device, like a smartphone or tablet computer. In fact, the use of the term controller is intended to represent a broad category of components that are well known in the art.

Hence aspects of the systems and methods provided herein encompass hardware and software for controlling the relevant functions. Software may take the form of code or executable instructions for causing a controller or other programmable equipment to perform the relevant steps, where the code or instructions are carried by or otherwise embodied in a medium readable by the controller or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s) shown in the drawings. Volatile storage media include dynamic memory, such as the memory of such a computer platform. Common forms of computer-readable media therefore include for example: a floppy disk, a flexible disk, hard disk, magnetic tape, any other magnetic medium, a CD-ROM, DVD, any other optical medium, punch cards paper tape, any other physical medium with patterns of holes, a RAM, a PROM and EPROM, a FLASH-EPROM, flash memory, microSD card, USB thumb drive stick, any other memory chip or cartridge, or any other medium from which a controller can read programming code and/or data. Many of these forms of computer readable media may be involved in carrying one or more sequences of one or more instructions to a processor for execution.

It should be noted that various changes and modifications to the embodiments described herein will be apparent to those skilled in the art. Such changes and modifications may be made without departing from the spirit and scope of the present system and without diminishing its attendant advantages. For example, various embodiments of the systems and methods may be provided based on various combinations of the features and functions from the subject matter provided herein.

We claim:
1. An assembly for protection of a load cell for use in a peritoneal dialysis device, the assembly comprising;
 at least one load cell mounted on a bottom plate beneath a fluid bag tray;
 a base plate positioned above the bottom plate;
 at least two vertical down-travel guideposts disposed within the bottom plate and positioned proximate to the load cell;
 a down-protection spring mounted around each guidepost wherein each guidepost sits within a bushing mounted into the base plate; and,
 wherein the bushing is configured to permit the springs and corresponding vertical guideposts to travel in unison in a downward vertical direction as the spring is compressed and in unison in an upward vertical direction as the spring is released.

2. The assembly of claim 1, wherein the assembly further comprises a hard stop disposed on the base plate.

3. The assembly of claim 2, wherein the load cell contacts the hard stop before reaching a maximum safe downward overload on the load cell.

4. An assembly for protection of a load cell for use in fluid measurement for a peritoneal dialysis device, the assembly comprising;
 at least one load cell mounted on a bottom plate beneath a tray for receiving a fluid delivery bag;
 a base plate positioned above the bottom plate;
 at least two vertical up-travel guideposts disposed within a top plate and positioned on opposing sides of the load cell;
 an up-protection spring mounted around each of the guideposts between an intermediate location on the guidepost and the top plate; and,
 a hard stop disposed on the base plate.

5. The assembly of claim 4, wherein a locking nut disposed at a base of the vertical up-travel guideposts and beneath the base plate contact the hard stop before reaching a maximum upward overload on the load cell.

6. An assembly for protection of a load cell for use in a drain unit of a peritoneal dialysis device, the assembly comprising;
 a drain container tray or hook configured for supporting at least one drain container for receiving fluid;
 at least one load cell mounted to a bottom plate at one end of the load cell,
 a drain container having a weight that pushes or pulls down on an opposite end of the load cell;
 a base plate positioned above the bottom plate;
 at least one down stop cylinder disposed within a top plate above the load cell and positioned on either side of the load cell;
 at least two vertical down-travel guideposts disposed vertically beneath the bottom plate; and,
 a down-protection spring mounted around each guidepost between the bottom plate and a base plate.

7. The assembly of claim 6 wherein the assembly further comprises a hard stop disposed on the base plate.

8. The assembly of claim 7, wherein the down stop cylinders are configured to stop on the hard stop before reaching a maximum safe downward overload on the load cell.

* * * * *